United States Patent [19]

Capra et al.

[11] Patent Number: 6,063,905
[45] Date of Patent: May 16, 2000

[54] RECOMBINANT HUMAN IGA-J. CHAIN DIMER

[75] Inventors: J. Donald Capra; Jonathan M. Hexham, both of Dallas, Tex.; Leon N. Carayannopoulos, St Louis, Mo.; Edward E. Max, Bethesda, Md.

[73] Assignees: Board of Regents, The University of Texas System, Austin, Tex.; The United States of America as represented by the Department of Health and Human Services, Washington, D.C.

[21] Appl. No.: 08/779,597

[22] Filed: Jan. 7, 1997

[51] Int. Cl.[7] .......................... C12P 21/08; C07K 16/00; A61K 39/395; C12N 5/06
[52] U.S. Cl. .................... 530/387.3; 530/390.1; 530/387.1; 424/130.1; 424/133.1; 435/328
[58] Field of Search ............... 530/387.1, 387.3, 530/390.1; 424/130.1, 133.1, 136.1; 435/328

[56] References Cited

U.S. PATENT DOCUMENTS 5,698,679  12/1997  Nemazee ............................. 530/387.3

OTHER PUBLICATIONS

Carayannopoulos et al 1994 Proc. Natl. Acad. Sci. 91:8348–8352.

Quirakkoo et al 1996 Immunotechnology 2(3):219–228 Abstract Only.

Castilla et al., Interference of coronavirus infection by expression of immunoglobulin G (IgG) of IgA virus–neutralizing antibodies, *J Virol.*, 71(7):5251–5258, 1997.

International Search Report dated Apr. 27, 1998 (PCT/US98/00614) (UTFD:505P).

*Primary Examiner*—Yvonne Eyler
*Attorney, Agent, or Firm*—Arnold, White & Durkee

[57] ABSTRACT

Disclosed are compositions and methods of use that comprise engineered IgA antibodies that, when administered to a host are secreted across the epithelium into the mucosal barriers of the body providing external passive immunotherapy against agents such as viral, bacterial and eukaryotic pathogens. Also disclosed are mini antibodies comprising the minimal transcytosis domains.

102 Claims, 5 Drawing Sheets

RECOMBINANT HUMAN IGA-J. CHAIN DIMER

The government owns rights in the present invention pursuant to grant number AI 12127 from the National Institutes of Health.

BACKGROUND OF THE INVENTION

1. Field of the Invention

The present invention relates generally to the field of the humoral immune defense against pathogens that enter the body through mucosal surfaces. More particularly, it concerns the field of recombinantly produced dimeric IgA antibodies and the secretion of such antibodies into the mucosal secretions for protective immunity from external pathogens including viral, bacterial, bacterial toxins and macroscopic parasites.

2. Description of Related Art

The mucosal surfaces of the body represent the largest area of exposure of the body to external pathogens, 400 m$^2$ compared to only 1.8 m$^2$ of skin area (Childers et al., 1989). IgA is the immunoglobulin subclass primarily responsible for humoral immune protection at this large exposed surface. IgA can intracellularly associate with J-chain via a cysteine in the C terminal "tail" to form dimeric IgA (dIgA, Koshland, 1985) which can be bound by the polymeric immunoglobulin receptor (pIgR) and transported across mucosal epithelia (Mostov and Blobel, 1982; Underdown, 1990; Mostov, 1994) to be released as secretory IgA (sIgA). Therefore sIgA serves as the first line of humoral immune defense at mucosal surfaces (Underdown and Schiff, 1986).

IgA is a tetrameric protein comprising two identical light chains (κ or λ) and two identical heavy chains (α) which endow IgA with its biologically specific properties. In the human there are two IgA isotypes, IgA1 and IgA2, present as a result of the duplication and subsequent diversification of a large segment of the human heavy chain locus (Torano and Putnam, 1978, Putnam et al., 1979, Tsuzukida et al., 1979,). The overall domain structure of IgA appears to resemble IgG in that it contains three constant domains (Cα1–Cα3), with a hinge region between the Cα1 and Cα2 domains. All IgA isotypes (as well as IgMs) have an 18 amino acid "tailpiece" C-terminal to the CH3 domain not present on IgG which enables polymeric Ig formation (Garcia-Pardo et al., 1981, Davis et al., 1988).

Serum IgA is present in monomeric or polymeric forms, which are mostly dimers, though tetramers and higher polymers have been observed. Polymerization is unique to antibodies of the IgA and IgM isotypes and is mediated by the tailpiece in conjunction with the J chain, one molecule of which is present per dimer of IgA (Zikan et al., 1986). The J chain is a small glycoprotein (15 kD) component of polymeric IgA and IgM (Koshland, 1985). J chain contains six interchain disulfide bonds and two additional cysteine residues at positions 15 and 79 which form disulfide bonds to the penultimate cysteine of one heavy chain in each IgA monomer subunit (Bastian et al., 1992). Thus J chain bridges the two IgA monomers, while the other two tailpiece cysteine residues bind each other directly, stabilizing the dimeric molecule further.

Dimeric IgA (as well as polymeric IgM) is specifically bound by the pIgR, expressed on the basolateral surface of mucosal epithelial cells, and transported through these cells to be secreted at the mucosal surface. Secretory IgA (sIgA) retains most of the extracellular region of the pIgR, termed secretory component (SC), covalently bound to one of the IgA monomers (Underdown et al., 1977).

Studies in J chain knockout mice show that J chain is not absolutely necessary for IgA polymerization although it is much less efficient in the absence of J chain (Hendrickson, et al., 1995). In these mice levels of IgA in bile and feces were much reduced, as was the level of dimeric IgA in serum. Further investigation revealed that intestinal, mammary and respiratory secretions contained IgA in a predominantly monomeric form (Hendrickson et al., 1996), therefore J chain is not necessary for IgA secretion but appears to stabilize the interaction between secreted IgA and secretory component.

The structures on the pIgR which mediate the interaction with IgA have been partially identified as has the mechanism of association between IgA and pIgR. The pIgR is a 110 kD transmembrane glycoprotein with five immunoglobulin superfamily homology domains (I–V) in the extracellular region (Mostov et (et al., 1984, Eiffert et al., 1984). The primary site of interaction of pIgR with dIgA is in domain I (Frutiger et al., 1986), which participates in a high affinity ($10^8$ M$^{-1}$), non-covalent interaction (Kuhn and Kraehenbuhl, 1979). Further mapping of the dimeric IgA binding site within domain I of the pIgR has identified a peptide comprising residues 15–37 of human pIgR which binds dIgA (Bakos et al., 1991a). A mutational approach, based on modeling of the domain I sequence on known Ig variable domain structures, demonstrated that the loops in analogous positions to the three V region CDRs made up the dIgA binding site (Coyne et al., 1994). This suggests that the interaction of the pIgR with dIgA is similar to the interaction of antibody with antigen, or to be more precise, the interaction of a single V domain with antigen.

The second stage of the interaction between pIgR and dIgA involves covalent binding of domain V to the Fc of one of the subunits in dIgA (Lindh and Bjork, 1974, Cunningham-Rundles and Lamm, 1975). This single disulfide is formed between cys467 in domain V of secretory component and cys311 located in the Cα2 domain of a heavy chain in one IgA subunit (Fallgreen-Gebauer et al., 1993). Disulfide formation appears to be a late event in the secretion pathway and is not absolutely necessary for transcytosis (Chintalacharuvu et al., 1994, Tamer et al., 1995).

Protective antibodies of the IgA isotype have been documented against a wide range of human pathogens including viruses such as IIIV (Burnett et al., 1994) and influenza A (Liew et al., 1984), bacteria (Tarkowski et al., 1990, Hajishengallis et al., 1992) bacterial toxins and macroscopic parasites (Grzych et al., 1993). There are several mechanisms by which IgA exerts its antimicrobial effect and they may be divided into active (e.g. Fc receptor binding or complement activation) and passive (e.g. blocking of viral receptors for host cells or inhibition of bacterial motion) mechanisms.

A number of studies have demonstrated the association between strong mucosal IgA responses and protection against viral infection with rotavirus (Underdown and Schiff, 1986, Feng et al., 1994), influenza virus (Taylor and Dimmock, 1985, Liew et al., 1994), poliovirus (Ogra and Karzon, 1970), respiratory syncytial virus (Kaul et al., 1981), cytomegalovirus (Tamura et al., 1980) and Epstein-Barr virus (Yao et al., 1991). Secretory IgA is therefore, successful in preventing these viruses from gaining access to the body by blocking infection at the site of entry, namely the mucosal surface. Passive immunotherapy with intranasal IgG Fabs was protective against respiratory syncytial virus (Crowe et al., 1994), showing that the mere presence of neutralizing anti-viral antibodies, without any effector function, at the mucosal surface can prevent viral infection.

Due to its complex interactions with the host immune system the HIV virus has proved very difficult to contain once it has entered the body. Clearly a strategy based on exclusion of the virus from the body would be ideal. Mucosal IgA antibodies offer this possibility and have a key role in many viral infections. Since the mucosal surfaces of the body are the usual point of entry of the virus to the body it seems logical to concentrate some effort at developing this first line of anti-viral defense. There are several reports suggesting a protective role for passive immunization in patients with AIDS.

It has been observed that HIV-1 infected individuals had neutralizing antibodies and high titer anti-viral antibodies in contrast to AIDS patients, who had low levels of anti-viral antibodies (Karpas et al., 1988). Passive immunization of both ARC and AIDS patients had beneficial effects. Neutralizing anti-HIV antibodies have been produced using combinatorial libraries derived from long term asymptomatic HIV infected donors (Barbas et al., 1992 and 1993), suggesting a role for humoral immunity in limiting progression of HIV infection. Passive immunotherapy, using human anti-HIV sera, has been shown to delay the progression of disease in HIV-infected patients (Vittecoq et al., 1995). Vaccination studies in macaques have suggested that secretory IgA can play a major role in neutralizing HIV-1 (Bukawa et al., 1995). The relative roles of systemic and mucosal IgA in the anti-HIV response remains to be elucidated though neutralizing IgA antibodies are present in the serum of HIV infected patients (Burnett et al., 1994). The presence of sIgA antibodies in the saliva of HIV-1-infected individuals correlated well with asymptomatic HIV infection, whereas the patients with AIDS displayed reduced sIgA levels in saliva (Matsuda et al., 1994). In contrast, no such correlation was observed with the serum IgG in these individuals.

The presence of maternal serum IgA against HIV has proven to be of prognostic value in determining the materno-fetal transmission (Re et al., 1992). In this study mothers who gave birth to uninfected children had serum IgA against HIV, directed particularly against the gp24 protein. However the mothers of infected children did not possess this reactivity. It has been suggested that some materno-fetal transmission of the HIV virus occurs during the process of parturition (Livingston et al., 1995). Therefore the presence of this serum reactivity suggests that secretory IgA (sIgA) with this specificity may confer protection during the process of birth by neutralizing the HIV present in the birth canal. The type of IgA response to the virus seems to be specific in that IgA1 is preferentially expressed (Kozlowski et al., 1992) and perhaps this subclass of IgA, is more effective at combating the virus. These studies demonstrate the potential for antibodies in combating the disease and give rise to the hope that vaccination, in non-immunocompromised individuals, may elicit protective antibody-mediated immunity. Unfortunately, there is no immunotherapy available to treat the HIV at the mucosal surface, before it enters the body.

SUMMARY OF THE INVENTION

The present invention overcomes these drawbacks in the prior art by providing methods and compositions for providing protective immunotherapy at the mucosal surfaces of the body and that concurrently provide passive immunoprotection in the serum. The dimeric IgA antibodies may be produced by recombinant methods, in insect cells, for example, and formulated for administration to an animal or human subject. As a further aspect of the invention, the minimal IgA antibody for binding to the pIgA receptor is defined herein, and provides a method of more efficient delivery of pathogen neutralizing immunotherapy, or antipathogenic drug.

The present invention may be described in a broad aspect as a pharmacological composition comprising a recombinant dimeric IgA antibody wherein the antibody is immunoreactive with an infectious agent. The infective agent may be a virus, a bacteria or a eukaryotic pathogen such as a protozoan or a helminth, for example. The antigen recognition function of the compositions disclosed herein are those that recognize an antigen of an infective agent, or a toxin produced by a foreign agent such as a bacterial toxin, for example. The antigens are typically surface antigens that are available when the pathogen is intact, or in its infective form. Such antigens may also include eukaryotic adhesins, the binding of which would prevent adhesion to mucosal surfaces.

Pathogens against which the antibodies of the compositions disclosed herein may be viral and may include, but are not limited to, influenza A, B and C, parainfluenza, paramyxovirus, Newcastle disease virus, respiratory syncytial virus, measles, mumps, adenovirus, adenoassociated virus, parvovirus, Epstein-Barr virus, rhinovirus, coxsackievirus, echovirus, reovirus, rhabdovirus, lymphocytic choriomeningitis, coronavirus, poliovirus, herpes simplex, human immunodeficiency virus, cytomegalovirus, papillomavirus, virus B, varicella-zoster, poxvirus, rubella, rabies, picornavirus or rotavirus. Certain preferred compositions are immunoreactive with a human immunodeficiency virus, and may be immunoreactive with gp120 of HIV.

In addition to the anti-viral compositions, the immunotherapeutic compositions of the present invention may be anti-bacterial, or directed against a bacterial pathogenic agent or toxin. Representative bacteria would include, but are not limited to species of pneumococci, species of Streptococci, including but not limited to *Streptococcus pyogenes, Streptococcus agalactiae, Streptococcus equi, Streptococcus canis, Streptococcus bovis, Streptococcus equinius, Streptococcus anginosuts, Streptococcus sanguis, Streptococcus salivarius, Streptococcus mitis, Streptococcus mutans*, also viridans streptococci, peptostreptococci, various species of Enterococci, such as *Enterococcus faecalis, Enterococcus faecium*, species of Staphylococci such as *Staphylococcus epidermidis, Staphylococcus aureus*, also *Hemophilus influenzae, Pseudomonas aeruginosa, Pseudomonas pseudomallei, Pseudomonas mallei*, and other pathogen Pseudomonads, *Brucella melitensis, Brucella suis, Brucella abortus*, and related species, *Bordetella pertussis, Neisseria meningitidis, Neisseria gonorrhoeae, Moraxella catarrhalis*, Corynebacteria such as *Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi, Listeria monocytogenes, Nocordia asteroides*, various species of Actinomycetes, *Treponema pallidum*, various Leptospirosa, *Klebsiella pneumoniae, Escherichia coli*, species of Proteus, *Serratia marscesens* and related species, species of Acinetobacter, *Yersinia pestis, Francisella tularensis*, species of Enterobacter, species of Bacteriodes and of Legionella.

The compositions of the present invention may also be directed against a eukaryotic organism such as a protozoan or a helminth. Exemplary eukaryotes include, but are not limited to various species of Cryptosporitiuml, *Isospora belli, Toxoplasma gondii, Trichomonas vaginalis*, various species of Cyclospora, *Chlamydia trachomatis, Chlamydia psittaci* or *Chlamydia pnieumoniae*, for example.

The invention may also be described in a broad aspect as a method of inhibiting an infection in a subject by an infective agent comprising administering to said subject a dimeric IgA antibody immunoreactive with said agent in an amount effective to inhibit said infection. The methods of the invention as described herein will have applications in the fields of human medicine as well as in veterinary medicine. In the practice of the invention, it is preferable that the Cα3 domains of the antibody compositions are derived from the host species. The methods of the invention may be further defined as comprising the steps of obtaining genetic sequences encoding Ig heavy chain and light chain recognition sequences immunoreactive with an infective agent and fused to Cα3 domains including the tailpiece, obtaining a genetic sequence encoding an Ig J-chain, co-expressing the genetic sequences in a cell, preferably in an insect cell, to obtain a dimeric IgA antibody immunoreactive with the agent; and administering the IgA molecule to the subject. The infective agent to be inhibited may be a bacteria, a virus or a eukaryotic agent including a protozoan or a helminth. Representative species are as defined in the preceding paragraphs.

A certain broad aspect of the invention is an IgA antibody consisting essentially of a VH domain fused to a first IgA1 Cα3 domain including a tailpiece, a VL domain fused to a second IgA1 Cα3 domain including a tailpiece, and a J-chain, wherein the VL and VH domains constitute an antigen or hapten recognition site. These antibodies are also referred to herein as "mini IgA" antibodies. By consisting essentially of is meant that the antibodies include only the antibody domains shown herein to be essential for dimerization and for binding of the dimers to the pIgA receptor. The invention may be further defined as the dimers of the described minimal IgA antibodies formed by disulfide bonds between the monomers and the J-chains and across the tailpieces as shown in FIG. 3B.

A further aspect of the invention is the mini IgA antibodies as described in the previous paragraph, and preferably the dimeric antibodies dispersed in a pharmaceutically acceptable solution. Preferred antibodies may have the Cα3 domains of the host species, and particularly preferred for administration to humans are antibodies with the human Cα3 domains. Also preferred are antigen recognition sites wherein the antigen is a viral, bacterial or protozoan antigen. Exemplary species are as defined above.

In a broad aspect, therefore, the present invention includes the recombinant production of dimeric or polymeric IgA antibodies that are secreted into the mucosal surfaces of a subject when administered into the serum of the subject. The antibodies may be produced or identified by any means known in the art. In particular, an intact pathogenic organism, or a purified antigenic compound isolated or derived from any pathogenic organism may be used to produce or identify an antibody, or a "mini" antibody as described herein. The antibody is then produced in its dimeric form, dispersed in a pharmaceutical composition and then administered to a subject to afford protection at the mucosal barriers from the antigen presenting pathogen. In light of the present disclosure, one of skill in the art could, without undue experimentation, practice the invention in the treatment or inhibition of infection by any of the pathogens named herein or others for which the compositions and methods disclosed and described herein would be effective.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
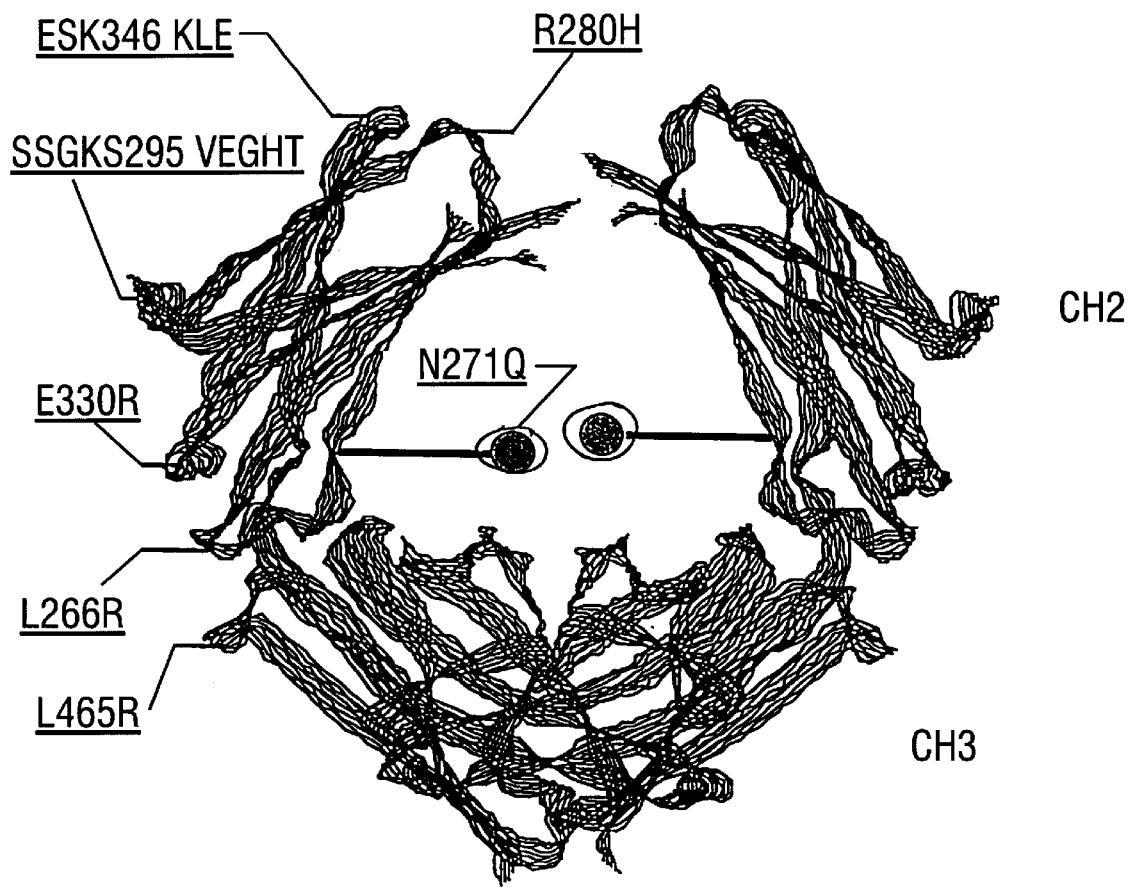
FIG. 1. An α-carbon ribbon trace of the three-dimensional structure of Fc region of human IgG1 (from Deisenhofer, 1981). The left hand heavy chain shows the putative positions of those IgA amino acids which have been targeted for mutational analysis. Mutations including ESK346, R280H, KLE, SSGKS295 AND VEGHT had no effect, E330R, N271Q, L266R and L465R completely abrogated binding to the Fcα receptor (Carayannopoulos, et al., 1996). The circles between the paired CH2 domains denote N-linked glycosylation sites. Numbering is according to Kabat and colleagues (Kabat, et al., 1991).

The present invention provides a method of producing and administering dimeric or polymeric IgA antibodies that are for useful in preventing or inhibiting infection by pathogens, and in particular, any pathogen that enters or exits the body through a mucosal barrier. The compositions of the invention are administered to a subject, such as an animal or a human and are subsequently, after a latent period of up to 24 hours, transported across a mucosal barrier. After active or passive transportation into the mucosa, the antibodies of the invention are available to inhibit an infection at that site. Because this is a method of passive immunity, it is understood based on the serum half lives of antibodies, that the protection may last for a period of several weeks and that the compositions may then be re-administered if the need persists. The invention provides, therefore, a method of inhibiting an infection prior to entry into the body, offering a first line of defense prior to exposure to the particular pathogen. Pathogens that may be inhibited from infecting a subject include, but are not limited to, viruses, bacteria, and macroscopic parasites such as protozoans.

The mucosal surfaces of the body offer an important advantage over serum as a site of immunological prevention or inhibition of disease, in that rather than responding to an infection that has already occurred, an immunological response at the mucosal surface prevents the infective agent from entering the body. Such a preventative method, as provided by the present disclosure, would be of dramatic benefit, not only in the prevention of sexually transmitted infections and maternal transmission of those diseases during birth, but also in the prevention of other infections that enter the body through mucosal surfaces such as the genitourinary tract, mouth, nasal passages, lungs, eyes, etc. in man and in domestic or non-domesticated animals.

The present invention would have applications therefore in the prevention of viral diseases that may enter or exit the body through the mucosal surfaces such as the following pathogenic viruses which are mentioned by way of example, influenza A, B and C, parainfluenza, paramyxoviruses, Newcastle disease virus, respiratory syncytial virus, measles, mumps, adenoviruses, adenoassociated viruses, parvoviruses, Epstein-Bar virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxviruses, rubella, rabies, picornaviruses, rotavirus and Kaposi associated herpes virus.

In addition to the viral diseases mentioned above, the present invention is also useful in the prevention or inhibition of bacterial infections, including, but not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides*, Bacteroides species, Actinomycetes species, *Treponema pallidum*, Leptospirosa species and related organisms. The invention may also be useful against gram negative bacteria such as *Klebsiella pneumoniae, Escherichia coli*, Proteus, Serratia species, Acinetobacter, *Yersinia pestis, Francisella tularensis*, Enterohacter species, Bacteriodes and Legionelia species and the like. In addition, the invention may prove useful in controlling protozoan or macroscopic infections by organisms such as Cryptosporidium, *Isospora belli, Toxoplasma gondii, Trichomonas vaginalis*, Cyclospora species, for example, and for *Chlamydia trachomatis* and other Chlamydia infections such as *Chlamydia psittaci*, or *Chlamydia pneumoniae*, for example. Of course it is understood that the invention may be used on any pathogen against which an effective antibody can be made. In light of the present disclosure, one of skill in the art would be able to produce a composition of dimeric IgA antibodies immunoreactive with any such pathogen and would further be able to administer such a composition to a subject.

Of particular interest, would be a means of prevention of infection with the HIV virus by immune exclusion mediated by secretory IgA at the mucosal surface. The present invention demonstrates the ability to secrete dimeric IgA into the vaginal fluids and thus to potentially inhibit heterosexual HIV transmission, for example. This embodiment offers the benefits of a passive immunotherapy to prevent perinatal transmission of the virus as well as a method of inhibiting the sexual transmission of this disease in the general population.

As disclosed herein, the intravenous administration of dimeric IgA antibodies to macaques resulted in the presence of the secreted antibodies in the vaginal fluid. While the animal model described herein was originally developed to investigate the sexual transmission of HIV (Miller et al., 1989) this model is also directly applicable to the materno-fetal situation. Indeed the materno-fetal situation at parturition is uniquely suited to this approach because protection is only needed for a short time (i.e. the period of delivery). The observed time course of secretion of IgA in the vaginal fluid in the macaques would work well in a delivery situation particularly if labor was managed by timed induction of delivery. In this case materno-fetal transmission of HIV could be prevented by administration 24 hr prior to delivery of protective anti-HIV dimeric IgA antibody.

For example, the presence of maternal serum IgA against HIV has been shown to be of prognostic value in determining the materno-fetal transmission (Re et al., 1992). In this study 72% of mothers (n=22) who gave birth to uninfected children had serum IgA against HIV, directed particularly against the gp24 protein. However the mothers of infected children did not possess this reactivity. The presence of this serum reactivity suggests that a secretory IgA (sIgA) with this specificity may confer protection during the process of birth by neutralizing the HIV present in the birth canal. The type of IgA response to the virus seems to be specific in that IgA1 is preferentially expressed (Kozlowski et al., 1992) and this subclass of IgA may be more effective at combating the virus. These studies demonstrate the potential for antibodies in combating the disease and give rise to the hope that vaccination, in non-immunocompromised individuals, may elicit protective antibody-mediated immunity.

It is also understood that any reduction in viral load would be a favorable outcome as this would increase the effectiveness of anti-viral drugs, or even other antibodies such as IgG antibodies, which could be used in conjunction with this therapy. Although significant progress has been made recently in reducing rates of perinatal transmission of HIV with anti-viral drug treatments the possibility exists to reduce these rates further using the compositions and methods disclosed herein.

PASSIVE IMMUNOTHERAPY

In the preantibiotic era passive immunization was administered for several bacterial infections including pneumococcal pneumonia and *H. influenza* pneumonia. In pneumococcal disease it was essential to identify the infecting scrotype and obtain the appropriate type specific antiserum. There is no question that this therapy was effective. The problems that arose from using horse serum and the difficulty in precisely defining the serotype led to the abandonment of this procedure as soon as antibiotic therapy was introduced into clinical medicine.

In recent years, passive immunotherapy has been used for several viral diseases such as hepatitis A, hepatitis B, polio, etc., and the use of intravenous gammaglobulin has grown as its applications have expanded. There have been several clinical trials with human monoclonal antibodies in various infectious diseases that document not only efficacy but safety. It is contemplated therefore, that large amounts of high affinity human monoclonal antibodies to critical epitopes of an infective pathogen, such as the human immunodeficiency virus, for example, may be effective in either preventing infections or in actual therapy. Although the bulk of contemporary opinion in virology and immunology supports the prevailing paradigm that immunity to the human immunodeficiency virus is largely cellular in nature, a significant body of evidence in vaccine studies in animals (Kamani et al., 1989, Sawyer et al., 1990, Moore et al., 1991) exists that has argued for a pivotal role for the humoral immune system. In chronic viral infections antibodies may be critical at certain stages and as such, antibodies may play a crucial role in the initial control of HIV-1 infections. Most importantly, through the use of the present invention virus may be excluded from the body altogether, or at least the level of infection reduced significantly.

MUCOSAL IMMUNITY

Immunoglobulins mediate humoral immunity by attaching to foreign antigens and activating effector modalities (e.g. complement, granulocytes, cytotoxic T-cells, etc.) to destroy and clear the antigens and also by passive inactivation, exclusion or immobilization of pathogens. The antibody is thus a flexible adaptor linking the variable, antigen binding domain to the constant region, containing the Fc (Fragment crystallizable) region. Each of the five Ig isotypes possesses its own spectrum of effector systems with which it interacts via its Fc domain. The constant region isotype of the antibody is determined following T-cell mediated, Ig class-switching which endows a given antibody with the specific effector modalities of the new isotype. Due to the immunological and clinical relevance of immunoglobulin-effector interactions, antibody structure/function is the subject of intense research (reviewed in Burton and Woof, 1992).

The mucosal surfaces of the body represent the largest area of exposure of the body to external pathogens and as such are the primary site of entry of pathogenic organisms (Childers et al., 1989). The polymeric antibodies (IgA and IgM) are secreted at the mucosal surfaces of the body where they form the first line of humoral immunological defense against external pathogens. IgA is the immunoglobulin subclass primarily responsible for humoral immune protection at this large exposed surface (Underdown and Schiff, 1986). Secretion of IgA and IgM occurs by a unique process termed transcytosis, mediated by the polymeric immunoglobulin receptor (pIgR), expressed on the basolateral face of the mucosal epithelial cells. As many pathogens, including HIV, normally enter the body via the exposed mucosal surface, specific antibody delivered to this site has the potential to prevent entry of the pathogen to the body.

IgA associates with J-chain via a cysteine in the C terminal "tail" to form secreted dimers (Koshland, 1982) which are then specifically recognized by the polymeric-Ig receptor (pIgR) and transported across mucosal epithelia (Mostov and Blobel, 1982; Underdown, 1990). The IgA thus transported serves as the first line of humoral defense at mucosal surfaces (reviewed in Underdown and Schiff, 1986). IgA is also the target of specific receptors and proteases produced by a number of pathogenic bacteria in an effort to evade IgA-mediated immunity (Kilian et al., 1988). In addition to mucosal IgA, blood also contains a large quantity (average 2 mg/ml, Mestecky and McGhee, 1987) of predominantly monomeric IgA; this circulating pool is largely independent of the mucosal pool in humans (Jonard, et al., 1984).

IgA is known to bind to a recently cloned (Shen et al., 1989; Monteiro et al., 1990; Maliszewski et al., 1990) Fcα receptor (mFcαR) on the surface of eosinophils (Monteiro et al., 1993), neutrophils (Weisbart et al., 1988), and monocyte/macrophages (Monteiro et al., 1990), thus triggering effector responses. B-lymphocytes and T-lymphocytes possess surface receptors for Fcα through which immunoregulatory signals are thought to be transmitted (Kurita et al., 1986). A receptor specific for sIgA, distinct from the FcαR, has been identified on eosinophils which may have a role in eosinophil activation and degranulation during the inflammatory response (Lamkhioued et al. 1995). IgA is also thought to activate complement through the alternative pathway (Lucisano-Valim and Lachmann, 1991).

Due to these functional properties, IgA not only plays a role in host defense against extracellular viruses and bacteria, but is also potentially critical for neutralization of intracellular viruses in tissues expressing pIgR (Mazanec et al., 1992), and destruction of helminths, protozoans and other eukaryotic parasites (Grzych et al., 1993). Several immunological disease processes also are mediated by IgA including IgA glomerulonephritis (Clarkson et al., 1984) and possibly the exacerbation of allergic asthma (Popper et al., 1982; Kitani et al., 1985). Each of the above-mentioned properties of IgA depends on the ability of effector molecules such as pIgR, C3 and the mFcαR to recognize specific sites on the surface of the Fcα protein.

Some of the structures on the pIgR which mediate the interaction with IgA have been identified, as has something of the mechanism of association. The pIgR is a transmembrane glycoprotein with five immunoglobulin superfamily homology domains (I–V) in the extracellular region (Mostov et al., 1984, Eiffert et al., 1984). The primary site of interaction with dIgA is the non-covalent binding of pIgR domain I (Frutiger et al., 1986) which is a high affinity ($10^8$ $M^{-1}$), non-covalent binding site for sIgA (Kuhn and Kraehenbuhl, 1979). Further mapping of the dimeric IgA binding site within domain I of the pIgR has identified a peptide comprising residues 15–37 of human pIgR which binds dIgA (Bakos et al., 1991a). This peptide showed high inter-species conservation and was also identified by a monoclonal antibody which was able to inhibit binding of dIgA to pIgR (Bakos et al., 1991a and b). In these studies the affinity of the interaction of the peptide with dIgA was about 100 fold lower than with the intact molecule. Similarly the specificity of the interaction was reduced such that binding of monomeric IgG to the peptide was now detectable though at lower affinity than dIgA and pIgM binding. A deglycosylated form of the pIgR molecule was still able to bind dIgA. These observations demonstrate that while this peptide may make up a central part of the binding site there are other regions of domain I which make important contributions to dIgA binding.

The association of IgA with the pIgR appears to be a two stage process (Mestecky and McGhee, 1987) the first being the binding of dIgA to domain I as discussed above. The second stage of the interaction between pIgR and dIgA involves covalent binding of domain V to the Fc of one of the subunits in dIgA (Lindh and Bjork, 1974, Cunningham-Rundles and Lamm, 1975). This single disulfide is formed between cys467 in domain V of secretory component and cys311, located in the Cα2 domain of a heavy chain in one IgA subunit (Fallgreen-Gebauer et al., 1993). This disulfide formation appears to be a late event in the secretion pathway and is not absolutely necessary for transcytosis (Chintalacharuvu et al., 1994).

Crucial to progress in the field of Fc structure/function have been the various in vitro expression systems which allow the production of immunoglobulins incorporating experimental sequence alterations. These systems have facilitated the elucidation of complement- and/or Fc receptor-binding sites on IgM, IgG and IgE (Burton and Woof, 1992). The baculovirus system (as described by Summers and Smith, 1987) allows production of mutant antibodies (as described by Hasemann and Capra, 1990; 1991) as well as combinatorial expression of immunoglobulin with other polypeptides (e.g. J chain, chaperoning, etc.) much more rapidly than with stably-transfected mammalian lines. A baculovirus system for production of immunologically and functionally authentic human IgA specificity for the arsonate hapten has been developed (Carayannopoulos, et al., 1994). The chimeric IgA generated was correctly assembled into heavy-chain:light-chain heterodimers, N-glycosylated and secreted by the insect cells, furthermore, when coexpressed with a human J-chain, the antibodies were able to assemble into dimers. The recombinant protein was authentic as judged by antigen-binding, recognition by monoclonal antibodies and complement fixation via the alternative pathway. The molecule also binds to the Fcα receptor and pIgR and expression of various mutant IgA molecules in this system has recently enabled the mapping of the binding sites of these two molecules on IgA (Carayannopoulos et al., 1996; Hexham et al., 1996). Thus the important effector functions of the molecule, namely Fcα binding, resulting in clearance of IgA immune complexes and pIgR receptor binding, leading to mucosal transport are preserved in these recombinant antibodies.

The main function of IgA is to mediate humoral mucosal immunity (Underdown and Schiff, 1986). However, serum IgA also plays a role in systemic immunity. As stated above, a number of studies have demonstrated the association between strong mucosal IgA responses and protection against viral infection with rotavirus (Feng et al., 1994), influenza virus (Liew et al., 1994), poliovirus (Orga and Karzon, 1970), respiratory syncytial virus (Kaul et al., 1981), cytomegalovirt's (Tamura et al., 1980) and Epstein-Barr virus (Yao, et al., 1991). Murine rotavirus infection is thus prevented by anti-viral IgA antibodies, present in the mucosae, following a primary inoculation (Underdown and Schiff, 1986). In addition, passive immunotherapy with intranasal IgG Fabs was protective against challenge with respiratory syncitial virus (Crowe et al., 1994), supporting a role for anti-viral antibodies present at the mucosal surface in prevention of viral infection. In contrast, there appears to be little, if any, correlation between the levels of anti-viral IgG in serum and viral protection. Similarly, the protection of mice against influenza virus infection was found to correlate with the presence of sIgA in the lung mucosae and not with the serum antibody or cytotoxic T cell activity (Liew, et al., 1994). Clearly IgA is successful in preventing these viruses from gaining access to the body by blocking infection at the site of entry, namely the mucosal surface. Serum IgA dimers also have the potential to eliminate immune complexed antigen from the submucosal area and can thus provide a secondary line of anti-viral defense even if the mucosal surface has been penetrated (Kaetzel et al., 1991 and 1994).

ANTIBODIES

Means for preparing and characterizing antibodies are well known in the art (See, e.g., Harlow and Lane, *Antibodies: A Laboratory Manutal*, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition including the pathogen or an antigen derived from the pathogen of choice (either with or without prior immunotolerizing, depending on the antigen composition and protocol being employed) and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carboduimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by assaying blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit or sheep cells is also possible. The use of rats may provide certain advantages (Goding, 1986, pp. 60–61), but mice are preferred, with the BALB/c mouse being most preferred as this is most routinely used and generally gives a higher percentage of stable fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

MOLECULAR CLONING OF ANTIBODIES

An alternative strategy, i.e. a molecular cloning approach may be used to generate monoclonals. In the practice of this method, combinatorial immunoglobulin phagemid libraries may be prepared from RNA isolated from the spleen, hybridoma or even B cells using the polymerase chain reaction, or by any other method known in the art. This isolated RNA is then cloned into expression vectors for screening. The vector may express antibody fragments on the surface of a bacteria, or more preferably, the antibody fragment may be expressed on the surface of a bacteriophage. Such systems are described by McCafferty et al. (1990) and Chester et. al., (1994) in which antibody genes are cloned into an fd phage vector at the N-terminal region of the gene III protein, for example. The authors showed that a functional antibody is expressed on the surface of the bacteriophage. The phage are then screened by immunoassay against antigen, or against the desired pathogen, and may be isolated by immunoprecipitation or affinity chromatography.

Repertoires of VH and VL genes may be made as described by Winter et al. (1994) (incorporated herein by reference) and used in the practice of the present invention. In this approach, the polymerase chain reaction is used to amplify VH and VL genes from lymphocytes using primers matching the 5' and 3' ends of rearranged VH and VL genes. V genes may be amplified from both cDNA and genomic DNA, with back primers at the 5' end of the exon encoding the mature V-domain and forward primers with the J-segment. In addition, for amplifying from cDNA, primers are designed to hybridize to the leader exon and are paired with primers designed to prime within the constant region. Increased diversity may be obtained in the libraries by incorporating degeneracy in the primers or by using different primers for different families of V genes. In addition, unique restriction sites may be included in the primers to aid in cloning. The use of these techniques may be combined with immunization, so that the genes are amplified from lymphocytes or spleen cells of an immunized animal increase the levels of antibody genes that may be obtained.

In alternative embodiments, rearranged V genes may be isolated from human peripheral blood lymphocytes using family based primers to amplify VH Vκ and Vλ families (Winter et al., 1994). The combination of these genes provides a large number of antibodies with novel specificities that can be screened against a variety of pathogens to obtain the secretory antibodies of the present invention. Also, synthetic libraries may be constructed by randomizing the H3 loop combined with a fixed light chain.

Of particular use in an embodiment of the present invention is S1-1, a human monoclonal antibody produced by a hybridoma derived from the spleen of an HIV sero-positive patient. This antibody may be used as part of a drug/antibody delivery system for passive immunotherapy for HIV. This IgG1/γ immunoglobulin has been shown to bind to the CD4 site on the surface glycoprotein, gp120, and to neutralize multiple virus strains, including HIV/IIIB, MN, SF2, and RF (Lake et al., 1992). It is also active against most primary isolates that have been analyzed by the inventors.

It is also an aspect of the invention that cloned antibodies may be mutated by site directed or random mutagenesis and screened for affinity of binding in order to obtain novel antibodies with increased binding to any of the pathogens described herein. In addition, a mixture of antibodies with a variety of binding affinities against the same or various antigens displayed by a particular pathogen may be useful in certain specific embodiments.

Thus, in light of the present disclosure, one may construct IgA molecules with anti-HIV specificity. The variable region genes for several anti-HIV antibodies have been cloned and sequenced and a vector has been constructed to express one of these antibodies (S1-1) as an IgA1 dimer in complex with J chain in the baculovirus system as described herein. A further use of these cloned antibodies will be the use of antibody engineering to generate antibodies containing IgA Fc regions with improved effector functions for expression in the baculovirus system. A similar approach is being employed in the anti-tumor field where dimeric IgA against carcinoembryonic antigen is under evaluation for in vivo carcinoma localization and possible therapy (Tersikh et al., 1994).

BACULOVIRAL EXPRESSION OF RECOMBINANT DIMERIC IgA

An advantage to using insect cells which utilize recombinant baculoviruses for the production of the antibodies of the present invention is that the baculovirus system allows production of mutant antibodies as well as combinatorial expression of immunoglobulin with other polypeptides, for example J chain and chaperonins among others, much more rapidly than stably transfected mammalian cell lines. In addition, insect cells have been shown to correctly process and glycosylate eukaryotic proteins which prokaryotic cells do not. Finally, the baculovirus expression of foreign protein has been shown to constitute as much as 50–75% of the total cellular protein late in viral infection, making this system an excellent means of producing milligram quantities of the recombinant dimeric IgA antibodies.

The use of the baculovirus *Autographia californica* nuclear polyhedrosis virus (AcNPV) and recombinant viral stocks in *Spodoptera frugiperda* (Sf9) cells to prepare large quantities of protein has been described by Smith et al. (1985), Summers and Smith (1987). A preferred method of preparing recombinant dimeric IgA is through the expression of DNA encoding recombinant dimeric IgA via the baculoviral expression system in Sf9 insect cells.

In general, recombinant IgA antibodies can be prepared by isolating DNA fragments corresponding to the heavy and light chain variable (V) regions of MAb and joining them to each other by any one of the standard methods known to those of skill in the art and described by Sambrook et al. (1989) and O'Reilly et al. (1992). These recombinant DNA fragments can then be inserted into baculoviral transfer vectors such that the genes of interest are inserted into the viral genome in lieu of the baculoviral polyhedron gene.

In a preferred embodiment of the present invention, DNA fragments corresponding to the heavy and light chain V regions of MAb 93G7 were amplified by PCR from plasmids pHγ1-360E and pHκ-360E, respectively. The oligonucleotide primers for these amplifications included a 5' Nco I site at the initiation codon and a 12 nucleotide antisense overlap with $C_\alpha$ at the 3' end. The coding regions of human Cα1 and Cκ were obtained from human peripheral-blood leukocyte RNA by RT-PCR™; in this case, the primers included a 12 nucleotide sense overlap with the appropriate V region at the 5' end and an Xba I site at the 3' end. The appropriate V anc C regions were joined by PCR™ overlap extension.

In a further embodiment of the present invention, a DNA segment comprising a J chain coding region was also isolated. A cDNA library from a human B-cell line was screened with a 1.6 kb Xba I fragment which included exons 3 and 4 from the human genomic J chain gene (Max and Korsmeyer, 1985). A clone encoding the 137 amino acid mature protein predicted from the previously characterized genomic clone (Max and Korsmeyer, 1985) as well as a 22 amino acid N-terminal signal peptide was obtained.

The isolated DNA fragments which encode the preferred genes were then inserted into the baculovirus transfer vectors. A preferred transfer vector of the present invention is based on pAc360. The DNA fragments were digested, purified and ligated into the unique Nco I and Xba I sites in pH-360EX (Haseman and Capra, 1990) using standard techniques known to those of skill in the art and described by Sambrook et al. (1989).

Recombinant plasmid vectors (2–20 µg) were then cotransfected with linear wild-type AcNPV (about 4 µg) into Sf9 cells. Cotransfection is preferentially accomplished by using cationic liposomes which are commercially available, e.g. Invitrogen, as per manufacturer's directions, except that 0.25 µg of linear DNA is preferentially is used. If desired, the recombinant plasmid DNA can be purified prior to transfection using at cesium chloride gradient, or other standard means known to those of skill in the art, prior to cotransfection. It is a preferred embodiment of the present invention that the growth, plaque purification and titration of viruses are by the standard technique described by Summers and Smith (1987). For example, after transfection, the resultant viruses are screened visually to isolate insect cells containing occlusion-negative, recombinant viruses. Sf9 cells infected with occlusion-negative viruses can then be grown in the desired quantity and under appropriate conditions such that large quantities of the dimeric IgA antibodies are produced. For protein production, infected cells are maintained in spinner flasks at a density of $2 \times 10^6$ per ml.

Recombinant IgA antibodies of the present invention were isolated as follows: Cells supernatants were adjusted to 20 mM Tris-Cl, pH 7.5/10 mM EGTA/10 mM EDTA/1 mM phenylmethanesulfonyl fluoride and centrifuged at 90,000×g for 40 minutes. Antibodies were isolated from the resulting supernatant by precipitation with ammonium sulfate at 40% saturation. This fraction was either used directly in further protocols and analyses or further purified on p-azophenylarsonate (Ars)-sepharose before proceeding.

To produce an intact immunoglobulin, both heavy and light chains need to be expressed. To produce a dimeric IgA, a human J chain must also be expressed with the heavy and light chains. Three general strategies can be employed to achieve this triple expression. One such strategy is the infection of an insect cell by three recombinant viruses, containing the heavy, light or J-chain gene, respectively. Another is the bi- or tricistronic expression of two or possibly all three of the polypeptides from one transcription unit. However, Hasemann and Capra (1990) found that bicistronic expression of heavy and light chain genes did not produce authentic heterodimeric immunoglobulin. A third strategy is the creation of a recombinant virus with two polyhedrin promoters, each initiating transcription of, for example, either the heavy or light chain cDNA. This would be combined with the coinfection of another recombinant virus which, in this case, contains the J-chain gene. A true double-recombinant transfer vector was engineered such that two foreign genes were contained in a plasmid, in opposite orientations, to produce a functional heterodimer immunoglobulin (Hasemann and Capra, 1990). This final strategy successfully produced dimeric IgA when the heavy and light chains were coexpressed with human J chain (Carayannopoulos et al., 1994). The double recombinant transfer vector was engineered such that two foreign genes were contained in a plasmid, in opposite orientations, to produce a functional heterodimer immunoglobulin similar to that described by Hasemann and Capra (1990).

To determine that the recombinant viruses do contain the correct gene to produce dimeric IgA of the present invention with the heavy and/or light chains in the correct location and orientation, DNA sequencing of PCR amplified genes can be performed. To verify that the protein products of the virally infected Sf9 cells are the desired antibodies of the present invention, SDS-PAGE, Western blot, glycosylation and ELISA analyses are performed. Artisans skilled in the art will be familiar with these techniques which are described in Sambrook, et al. (1989). To further verify that the antibodies of the present invention are authentic, they are examined for their reactivity with several IgA1-specific MAbs, M4C11, M4D8, 2D7, and N1F2 for example, in ELISA analyses as well as their susceptibility to cleavage by *H. influenzae* IgA1 protease. Cleaved Fc regions are analyzed by Western blotting. Finally, to demonstrate the presence of dimeric Ig, samples are subjected to non-reducing SDS/PAGE on 40% gels followed by Western blotting.

The ability of antibodies of the present invention to fix complement component C3 is assessed essentially as described by Schneiderman et al. (1990) with the following alterations. Ars-BSA or Ars-gelatin is used to capture hapten-specific antibody and normal human serum is used as the source of complement. Deposited C3 is detected with sheep anti-human C3 (The Binding Site, San Diego, Calif.) followed by goat anti-sheep Ig G conjugated to alkaline pahophatase (Sigma, St. Louis, Mo.).

To assess the ability of recombinant IgA to recognize the mFcαR, resetting of Ars-derivatized IgA-coated erythrocytes by mFcαR+ cells is examined. HL-60 promyelocytic leukemia cells express mFcαR following treatment with 0.5 µM calcitriol for 5–7 days and thus are used in these analyses. Sheep erythrocytes (Colorado Serum, Denver Colo.) are derivatized with Ars exactly as described by Henry (1980) and then washed with Hank's balanced salts solution (HBSS). The haptenated erythrocytes are then coated with sensitized antibody or random serum Ig (in HBSS). Rosetting is assessed as described by Shen el al. (1989). Induction of mFcαR on HL-60 cells is checked by standard flow cytometry using the My43 (IgM) anti-mFcαR MAb and by immunoblotting using a distinct IgG-class MAb (Monteiro et al., 1992). The dimeric IgA of the present invention specifically mediated resetting between HL-60 cells and Ars-coated erythrocytes.

PREPARATION OF RECOMBINANT DIMERIC IgA

A significant obstacle to an understanding of the IgA system has been the difficulties encountered by several investigators in defining the effector functions mediated by the Fc part of the molecule (Clackson et al., 1984). However recent progress in the inventors' laboratory (Carayannopoulos et al., 1994), has provided a means of answering some of the fundamental molecular questions about IgA. The heavy chain and light chain variable regions of the molecule, with specificity for the arsonate hapten, were cloned from a murine hybridoma as described previously (Hasemann and Capra, 1990). The coding regions of human Cαl and Cκ were obtained from human peripheral-blood leukocyte RNA by reverse transcription followed by PCR as previously described (Tuaillon et al., 1993). The appropriate variable and constant regions were then joined by PCR overlap extension (Horton et al., 1990). The human J chain clone was obtained from a human B cell line by screening with a genomic J chain sequence (Max and Korsmeyer, 1985). These genes were first cloned into baculovirus transfer vectors from which recombinant baculoviruses were produced using standard methods (Sambrook et al., 1989, O'Reilly et al., 1992). Coinfection of Sf9 cells (*Spodoptera frugiperda*) with recombinant baculoviruses facilitates the expression of multi-subunit protein complexes in milligram amounts. The power of the system is that IgA heavy chain, light chain and J chain may be expressed singly or in combination, thus allowing the production of many different versions of multi-subunit proteins (Potter, et al., 1993a; Potter, et al., 1993b). Mutational analysis is rapid because only the heavy chain construct need be altered, the light chain and J chain constructs remaining constant.

Binding of recombinant baculoviral IgA to the FcαR expressed on calcitriol-treated HL60 cells (a human promyelocytic cell line) has already been demonstrated using a resetting assay (Carayannopoulos et al., 1994). Briefly, hapten-coated erythrocytes are incubated in the presence of recombinant IgA or non-antigen specific IgA and the HL60 cells. In the case of the anti-arsonate IgA, clusters or rosettes of erythrocytes form around the HL60 cells, whereas binding to the HL60 FcαR, the control IgA or underivatized erythrocytes fail to give rosettes. A mutant, aglycosylated IgA does not interact with the Fcα receptor in this assay (Carayannopoulos et al., 1994). These studies have been extended by constructing further mutant IgA molecules, in which the human IgA constant domains have been swapped with the corresponding domains from human IgG (Carayannopoulos et al., 1996). Using this approach the presence of the Cα2 and the Cα3 (VGAA mutant) domains has been shown to be necessary for FcαR binding (see Table 1). An aglycosylated mutant in which N271 was mutated to glutamine, failed to bind the FcαR (FIG. 1). A comparison of the IgA1 Fc sequence with the homologous IgG1 Fc sequence, whose structure is known (Deisenhofer, 1981), suggested that a solvent-exposed loop in the Cα2 domain, containing N271, was involved in FcαR binding. This was confirmed by targeting point mutations to various residues as shown in FIG. 1. Mutation of the exposed L266, present in this loop four amino acids N-terminal to the glycosylation site, to arginine, also abolished binding. Mutation of E230, analogous with the catabolic site of IgG, present in a loop above the L266-containing loop, to arginine had no effect. Furthermore, the hinge-proximal region of the Cα2 domain, analogous to the Fc binding site in IgG was not implicated in the binding of the FcαR, as judged by the lack of effect observed with mutation of R280 to histidine and by removal of hinge, which also had no effect. The region from the CH3 domain involved in FcαR binding was shown to be the loop containing L465, which when mutated to arginine abolished binding (see FIG. 1).

To identify the minimum structural unit involved in FcαR binding, the loops involved from Cα2 and Cα3 domains are grafted onto the VAGA and VAAG mutants respectively (Table 1). 93G7 represents the murine VH region with specificity for arsonate (Hasemann and Capra, 1990). Binding to the FcαR was assessed by rosetting as described in Carayannopoulos, et al. (1996). The design of small molecules with Fcα receptor binding activities may provide a useful addition to existing antibody and drug approaches.

Table 1. Effect of IgA/IgG constant domain exchange on binding of IgA to the polymeric immunoglobulin receptor.

| V region | CH1 | CH2 | CH3 | Tail | Designation | Binding |
|---|---|---|---|---|---|---|
| 93G7 | α | α | α | τ | VAAA (wtIgA) | YES |
| 93G7 | α | α | γ | | VAAG | NO |
| 93G7 | α | γ | α | τ | VAGA | YES |
| 93G7 | γ | α | α | τ | VGAA | YES |
| 93G7 | γ | γ | α | τ | VGGA | YES |
| 93G7 | γ | γ | γ | | VGGG (wtIgG) | NO |

DIMERIC IgA BINDING SITE

Figure 2:
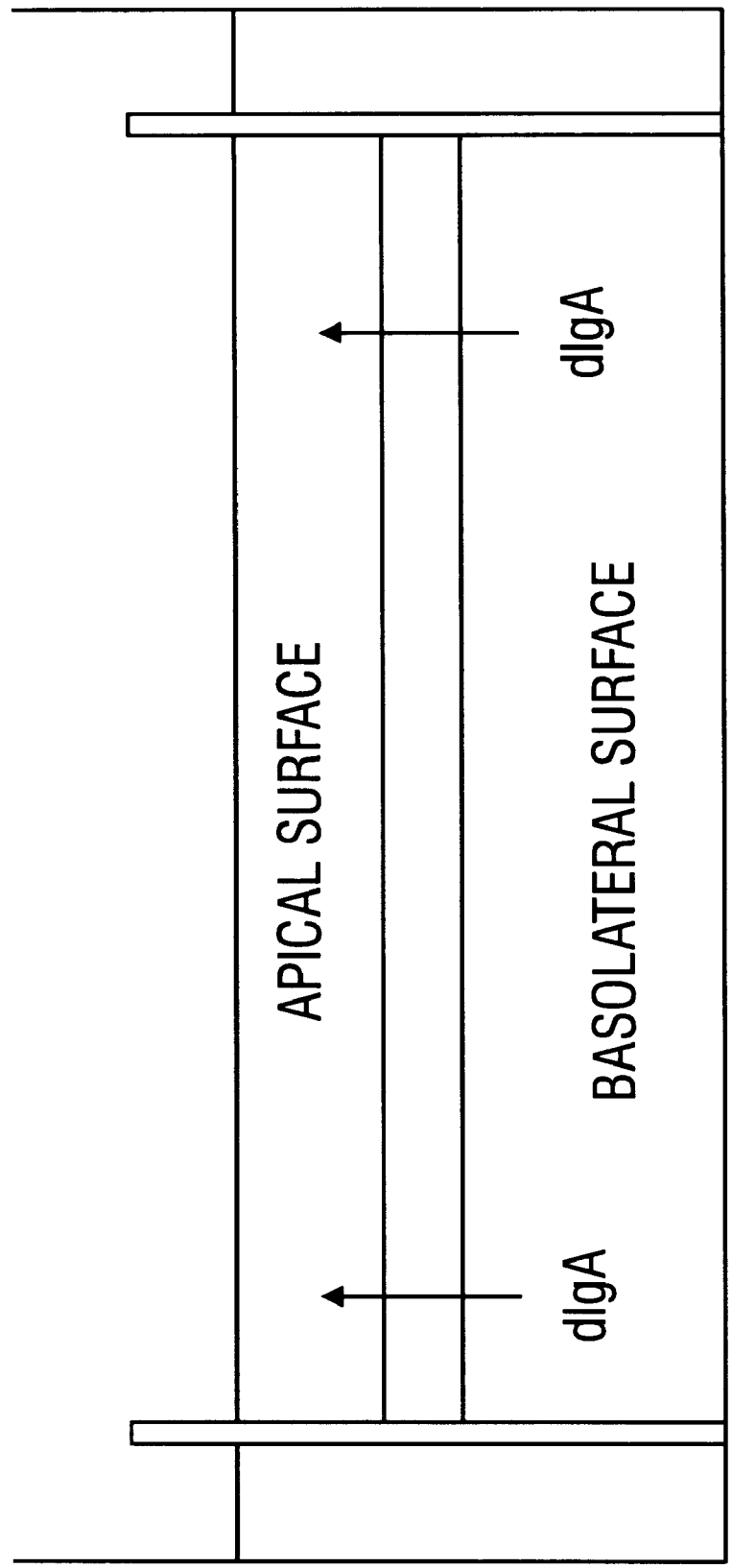
FIG. 2. MDCK cell system for transcytosis of dimeric IgA (dIgA) (Mostov and Deitscher, 1986). The poly Ig receptor expressing MDCK cells form a polarized monolayer with tight junctions when grown on a semi-permeable polycarbonate membrane in a tissue culture well. When dIgA is introduced into the lower (basolateral) chamber it is bound by the pIgR and transcytosed to the upper (apical) surface. Arrows indicate movement of active transport of dIgA.

An aspect of the present invention is the discovery of the minimal IgA dimer that is effective for transport by the pIgR through mapping of the binding site for the pIgR on dimeric IgA. The MDCK (Madin-Darby canine kidney) cell line, transfected with the pIgR, can be used in an in vitro transcytosis assay (Mostov and Deitscher, 1986) and has being used to assess binding and transcytosis of dIgA (FIG. 2). This is a polarized cell line, capable of forming monolayers with tight junctions, which when grown on a semipermeable support will transport dIgA from the lower (basolateral) to the upper (apical) chamber of a tissue culture well.

Domain swap mutants have been expressed as dIgA with J chain and examined for pIgR binding and transcytosis with this cell line. FACS analysis has been used to determine whether or not a given mutant will bind to the pIgR expressed on these cells. Cells are harvested with 10 mM EDTA in PBS and bound IgA is detected with an anti-human kappa chain FITC conjugate. Only dIgA, as operationally defined by IgA coexpressed with J chain, binds to the receptor, no binding of any monomeric IgA was observed with any of the mutants. When the panel of domain-swap mutants was expressed as dIgA and tested for pIgR binding only those with the CH3 domain derived from IgA were able to bind to the pIgR (Table 1). The ability of a mutant to be transported by the pIgR in the transcytosis assay also correlated with the expression of dimeric Ig, possessing the CH3 of IgA. The CH3 domain as expressed in this system, includes the IgA tailpiece which is essential for dimerization. The crucial determinants for pIgR binding have thus been localized to the domain including the CH3-tailpiece-J-chain complex. This may contain up to five polypeptide chains (ie. four IgA heavy chain CH3 domains and a J chain) or some combination of these chains.

PASSIVE IMMUNOTHERAPY COMPONENTS AND PREPARATION

Pharmaceutical compositions and the immunoglobulins that they deliver for passive immunotherapy are limited to temporary prophylaxis of susceptible individuals and to the immediate treatment of infections and toxicities. A discussion of passive immunity and immunizing agents may be found in *Remnington's Pharnmacelitical Sciences*, 18th Ed., pp. 1389–1404, 1990). The immunity provided by these means is not long lasting and the immunoglobulins provided by the vaccine leave the body tissues and fluids of the host within a comparatively short period of time, usually after one to two weeks, either by utilization by binding to the pathogen or by metabolism by the host's body. Thus, the administration of an antibody for passive immunity should be during the critical period immediately after or just prior to the predicted exposure to the pathogen or toxin such that the immunoglobulins are present when immunity is most urgently required.

The percentage of active compound in any pharmaceutical preparation is dependent upon both the activity of the compound, in this case an antibody(ies), and its concentration in the preparation. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injection is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, phenylmecuric nitrate, m-cresol and the like. In many cases, it will be preferable to use isotonic solutions, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterile filtration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The term also denotes that the compositions and additives cause no allergic or other undesired reaction when administered to a subject. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

DELIVERY OF FORMULATIONS

The formulations of the present invention may be conventionally administered parenterally, by injection, for example, either subcutaneously or intramuscularly. Additional formulations which are suitable for other modes of administration include suppositories and, in some cases, oral or aerosol formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The antibodies may be formulated as neutral or salt forms. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In many instances, it will be desirable to have multiple administrations of the antibodies, usually not exceeding six, more usually not exceeding four and preferably one or more, usually at least about three. The administrations will normally be at from one to twelve week intervals, more usually from one to four week intervals. Periodic re-administration will be desirable with recurrent exposure to the pathogen or toxin. For example, an HIV positive mother would be re-inoculated prior to parturition from a second pregnancy.

Dosages commonly used for formulations that provide passive immunity are in the range of from 0.5 ml to 10 ml per dose, preferably in the range of 2 ml to 5 ml per dose. Repeated doses to deliver the appropriate amount of active compound are common. Both the age and size by weight of the recipient must be considered when determining the appropriate dosage of active ingredient and volume to administer.

The course of the treatment may be followed by assays for antibodies for the supernatant antigens. The assays may be performed by labeling with conventional labels, such as radionuclides, enzymes, fluorescers, and the like. Samples for assaying may be serum samples, or they may be obtained from any mucosal surface, or body fluid, such as saliva, sputum, vaginal wash or expectoration. These assay techniques are well known and may be found in a wide variety of patents, such as U.S. Pat. Nos. 3,791,932; 4,174,384 and 3,949,064, as illustrative of these types of assays.

ANTIBODIES WITH MINIMAL pIgR RECOGNITION SITES

Figure 3A:
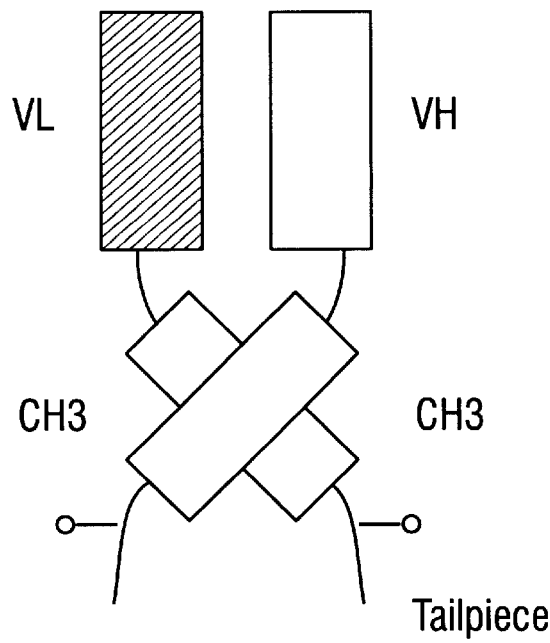
FIG. 3A and FIG. 3B. Construction of arsonate-specific "mini-IgA" monomer (FIG. 3A) and dimer (FIG. 3B) molecules. Each "muni-IgA" monomer contains two polypeptide chains, an arsonate-specific VH domain fused to a human IgA1 Cα3 domain and similarly an arsonate-specific VL domain fused to a human IgA1 Cα3 domain. Dimerization is achieved as in the native molecule with the tailpieces forming disulfide bonds to each other and the J chain (Bastian et al., 1992).
Figure 3B:
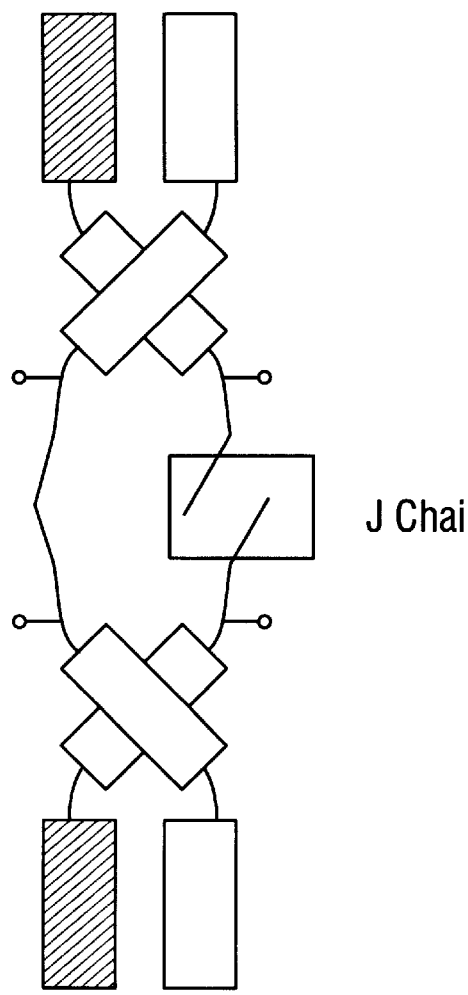
Figure 4:
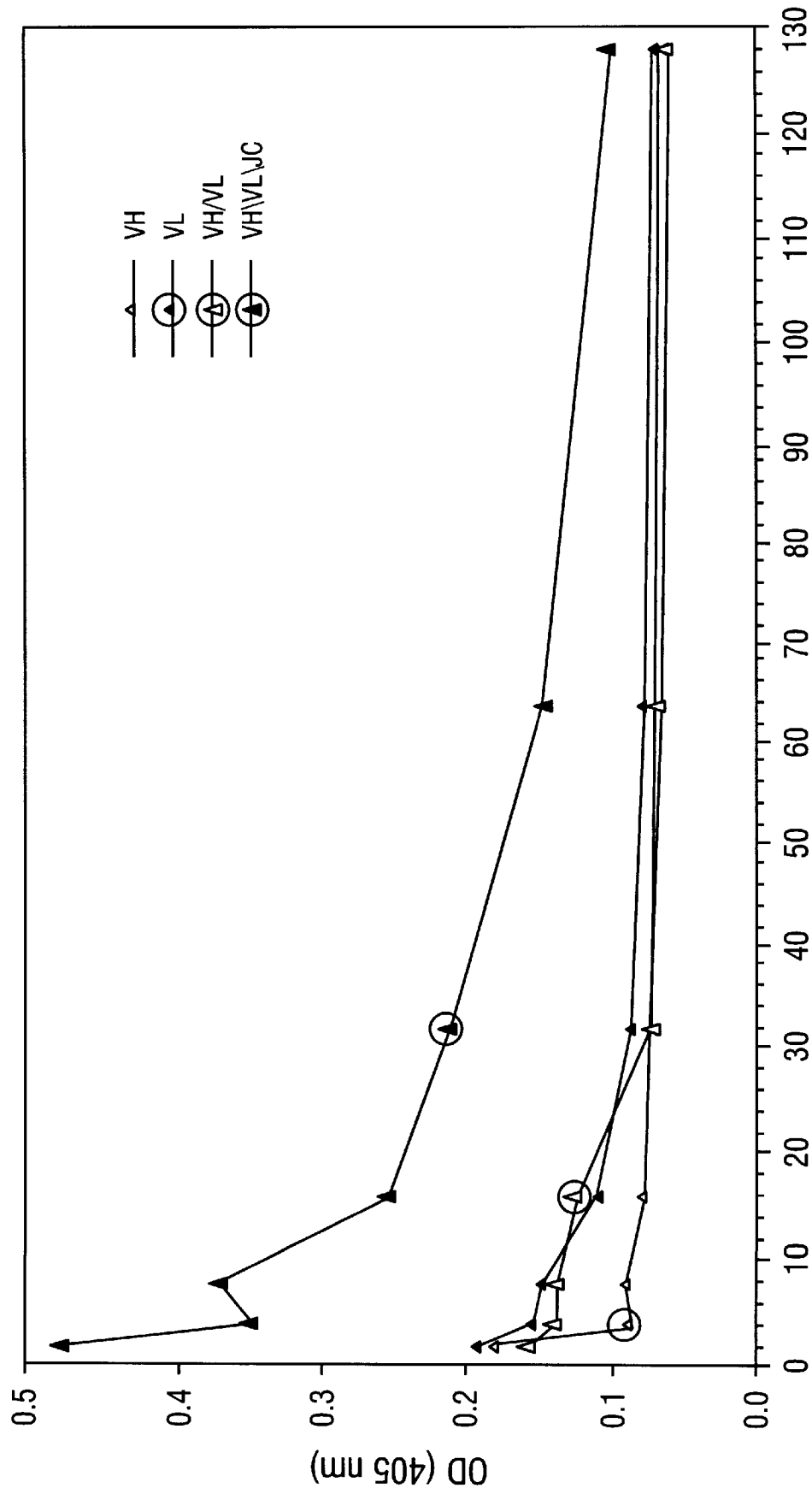
FIG. 4. Binding of "mini-IgA" molecules to arsonate hapten in ELISA following expression in baculovirus. The VH-Cα3 and VL-Cα3 fusion proteins were expressed singly, together, or in combination with J chain. Only with J chain coexpression was significant binding observed.

In an effort to conclusively identify the Cα3 domain, tailpiece and J chain as the minimal binding unit for the pIgR a "mini-IgA' dimer molecule was constructed and expressed using the baculovirus system (FIG. 3B). The molecule comprises the arsonate-specific VH and VL domains each fused to a human IgA1 Cα3 domain (including tailpiece). These two polypeptide chains have been successfully expressed in baculovirus, as indicated by Western blotting. When coexpressed with J chain to produce the "mini-IgA" dimer molecule hapten binding specificity is retained (FIG. 4).

IMMUNOASSAYS

Certain immunoassays may be used in the practice of the present invention and these include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and other solid support immunoassays known in the art. Immunohistochemical detection using tissue sections and radioimmunoassays (RIA) are also particularly useful. However, it will be readily appreciated that detection is not limited to such techniques, and Western blotting, dot blotting, FACS analyses, and the like may also be used.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modles for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Vaginal Secretion of dIgA antibodies

Figure 5:
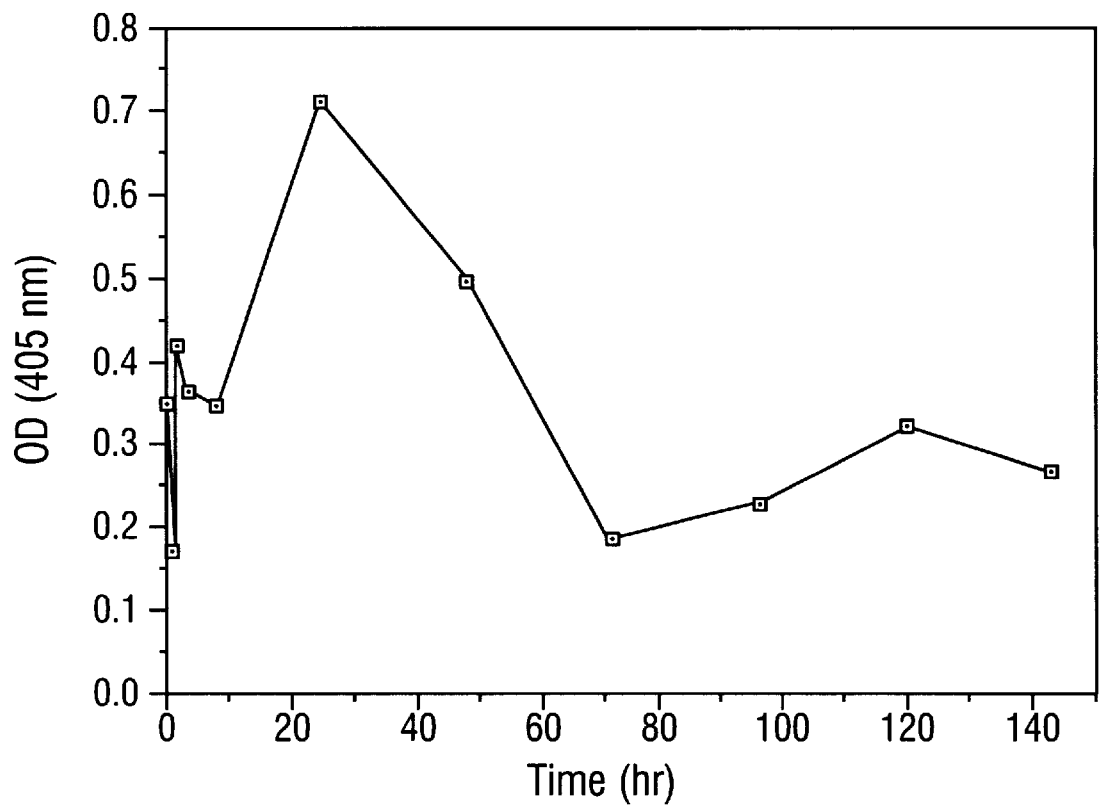
FIG. 5. Analysis of macaque vaginal secretions for anti-arsonate antibody activity following intravenous administration of human anti-arsonate IgA1 dimers.
Figure 6:
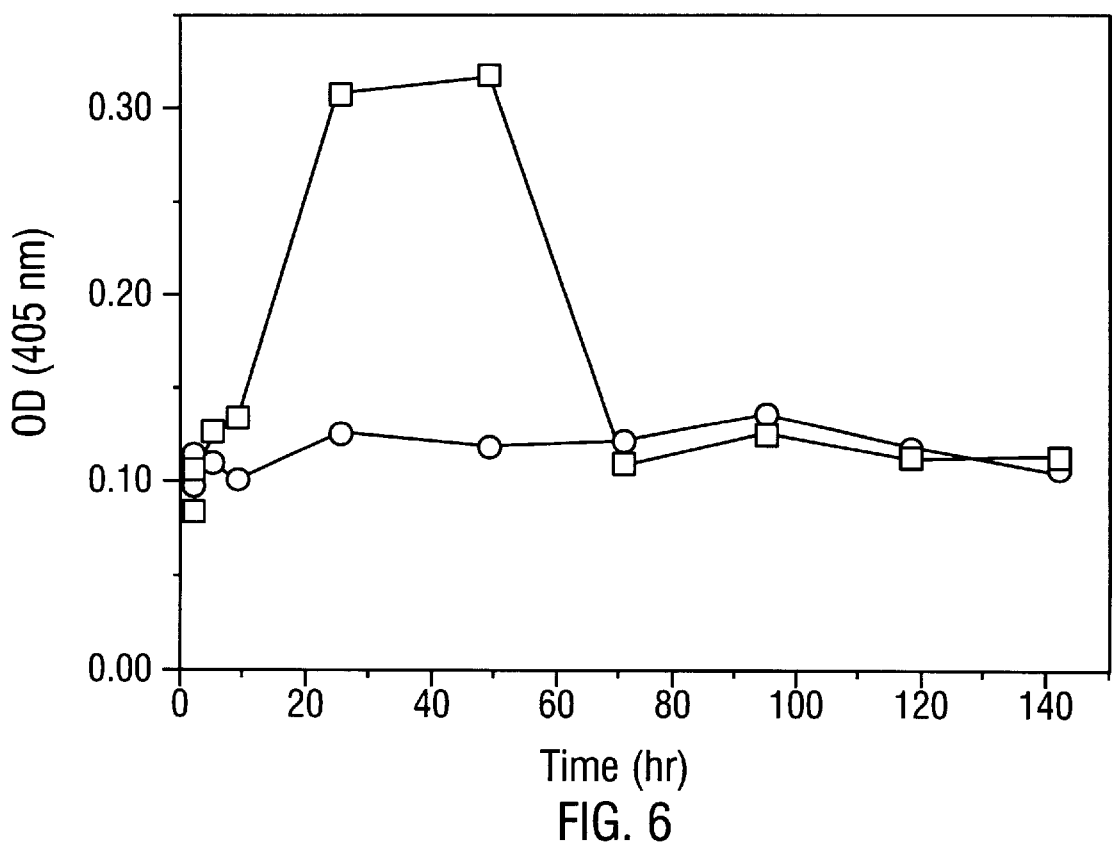
FIG. 6. Analysis of macaque vaginal secretions for anti-arsonate antibody activity following intravenous administration of human anti-arsonate IgA1 dimers. Analysis was carried out following a preincubation with either arsonate-BSA conjugate (filled circles) or BSA alone (filled squares).

A large amount (1 mg) of J chain-containing IgA1 dimer specific for the arsonate hapten was purified using a baculovirus expression system. Antibody from 0.5–1 liter cultures of IgA-expressing High five insect cells, grown in serum free (Ex-cell 405) medium, was subjected to affinity purification on arsonate-derivitized cyanogen bromide SEPHAROSE 6B. The material was eluted from the column with 0.5 M arsanillic acid and dialyzed extensively (10–12 changes over several days) against phosphate buffered saline to remove the antigen. The dialyzed material was concentrated by pressure filtration on an Amicon YM 30 membrane. The antibody was checked for purity and activity by SDS-PAGE and ELISA, and pIgR binding was confirmed by FACS on MDCK cells. Purified antibody was filter sterilized and tested for endotoxin. The antibody (500 mg in 3 ml) was injected intravenously into a rhesus macaque. Samples of serum and vaginal washes were taken 20 minutes prior to the injection then at intervals afterwards. This material was then subjected to arsonate-specific ELISA (FIG. 5), and competitive ELISA where soluble arsonate-BSA was used to inhibit the binding of the antibody to the arsonate-coated plate (FIG. 6).

The data show that antigen specific IgA is transported to the vaginal secretions 24 to 48 hrs post-injection. The one day lag between injection and appearance of the antibody at the mucosal surface is presumably due to the time taken for the antibody to leave the circulation and accumulate in the submucosal space where it can then be transported by the pIgR transcytosis pathway.

Table 1 indicates binding of dimeric IgA/IgG constant domain exchange mutants to pIgR on MDCK cells as measured by FACS analysis. 93G7 encodes the murine VH region with specificity for arsonate.

EXAMPLE 2

Vaginal Delivery of Protective Anti-HIV Antibodies in an SHIV/Rhesus Macaque Model A primate model of heterosexual AIDS transmission based on inoculation of the genital mucosae of animals with SIV has been developed (Miller et al., 1989). This model has enabled the development and testing of protective vaccines against SIV for efficacy against genital inoculation of the SIV virus (Marx et al., 1993). The more recently developed SHIV disease model in rhesus macaques (Luciw et al., 1995), where the virus is a hybrid of SIV and HIV bearing the HIV gp120 molecule, offers the opportunity to test the effectiveness of anti-HIV antibodies of the IgA subclass in combating the spread of AIDS. This has profound implications not only for a limited program of passive immunization but also for mucosal vaccination if the IgA antibodies are proven to be efficacious at prevention of infection.

The SIV/macaque model of heterosexual transmission has recently been extended to include the SHIV recombinant viruses (Luciw, et al., 1995). SHIV has an advantage over SIVmac in that this recombinant virus has the HIV-1 env in place of the analogous SIVmac env. It is therefore possible, to apply HIV-1 env reagents to the SHIV infected macaques. The SIV/Macaque model of genital mucosal transmission of SIV is well known and was developed in Dr. Marx's laboratory (Miller, et al, 1989). Indeed, it has been used to demonstrate protection against vaginal SIV transmission with a microencapsulated vaccine (Marx, et al., 1995).

The human monoclonal antibody S1-1 (Lake et al., 1992) expressed in the baculovirus expression system as an IgA recognizes gp120 in ELISA. The heavy and light chain genes encoding this antibody have been cloned into the baculovirus expression vectors with an IgA constant region and the expressed IgA antibody is active against gp120 in ELISA. The antibody is expressed as dimeric IgA on a large scale using serum-free medium and purified using affinity purification on the lectin jacalin which is specific for the O-linked sugar in the IgA1 hinge (Roque-Barriera and Campos-Neto, 1985).

As an aspect of the present invention, this antibody is used as an in vitro example to neutralize the SHIV33 strain which carries the HIV gp 120 env protein. The assay is 100 TCID50 of virus in rhesus PBMCS with irrelevant IgA and with HIV-specific IgA as controls. SIVP22 antigen production is measured at Day 0, 7, 10 and 14 as described (Marx et al 1993). Upon the finding of neutralizing activity, the IgA is intravenously administered to monitor protection of macaques against vaginal inoculation of SHIV. Twenty four hours following administration of the dIgA the macaques are inoculated vaginally with SHIV33 and levels of infection monitored over time by seroconversion, culture of SHIV from the peripheral blood and SHIV-specific PCR (Luciw et al., 1995).

To achieve higher levels of protection, other neutralizing antibodies as IgA dimers may be added to the innoculum to produce a cocktail of antibodies for the inhibition of viral transmission. Alternatively, mini-IgA molecules, bearing only the minimal motif for transport as described herein may offer the possibility of more efficient high level delivery of anti-HIV antibodies to the mucosal surface.

Table 2 shows the preliminary studies. Three of 3 female macaques were infected by non-traumatic application of $2.7 \times 10^4$ TCID50 of SHIV33 to the intact vaginal epithelium. SHIV was recovered from the peripheral blood of Rh 1412, 1414 and 1418. Two rhesus monkeys were persistently infected up to 140 day post-vaginal inoculation, the most recent time point tested. The third female inoculated with SHIV33 was infected on day 28, but gave a marginally positive signal by day 42. By repeatedly culturing samples from the animals during the first 60 days after inoculation the length of protection by pre-treatment with specific IgA is measured.

TABLE 2

| Days Post- Vaginal Inoculation | SHIV$_{162}$ | | | SHIV$_{33}$ | | |
|---|---|---|---|---|---|---|
| | Rhesus 1406 | Rhesus 1408 | Rhesus 1410 | Rhesus 1412 | Rhesus 1414 | Rhesus 1418 |
| 4 | − | − | − | − | − | − |
| 7 | − | − | − | − | − | − |
| 11(PBMC) | − | − | − | + | − | − |
| 11(LN) | − | − | − | + | − | − |
| 14 | − | − | − | + | + | − |
| 21 | − | − | − | + | + | − |
| 28 | − | − | − | +b | +b | + |
| 42b | −a | ±a | ±a | + | + | + |
| 56 | − | − | − | + | + | − |
| 140 | − | − | − | + | + | − |

Table 2 demonstrates isolation of SHIV from the blood of vaginally inoculated rhesus macaques. Virus infection was detected by co-cultivation of Rh PBMCs with CBMx174 cells as reported (Marx et al 1993). a—3 of 3 SHIV$_{162}$ inoculated were PCR positive on day 142. b—Sero converted by SlVmac Western Blot. Vaginal dose—SHIV$_{162}$= $4.5 \times 10^4$ TCID50 and SHIV33=$2.7 \times 10^4$ TCID50. PBMC—Peripheral Blood Mononuclear Cells. LN—Inguinal Lymph Node.

After the kinetics of neutralization are known, 4 macaques are pre-treated with HIV—env specific IgA and challenged with $10^4$ TCID50 of SHIV33 by the vaginal route. This is sufficient virus to infect all animals. Four controls are treated with a control IgA. All 8 macaques are challenged with 1 ml of SHIV33 titered stock. Should any animals resist infection, the controls and the treated animals will be reimmunized and vaginally inoculated a second time. Repeated exposures of immunized animals and controls has been used successfully to show protection (Marx et al 1993).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bakos, M., Kurowsky, A. and Goldblum, R. M. (1991) Characterization of a critical binding site for human polymeric Ig on secretory component. *J. Immunol.* 147, 3419–3426

Bakos, M., Kurowsky, A., Woodward, C. S., Denney, R. M. and Goldblum, R. M. (1991b) Probing the topography of free and polymeric Ig-bound human secretory component with monoclonal antibodies. *J. Immunol.* 146, 162,–168

Barbas, C. F., Bjorling, E., Chiodi, F., Dunlop, N., Cababa, D., Jones, T. M., Zebedee, S. L., Persson, M. A. A., Nara, P. L., Norrby, E. and Burton, D. R. (1992) Recombinant human Fabs neutralise human type 1 immunodeficiency virus. *Proc. Natl Acad. Sci. USA* 89, 9339–9343

Barbas, C. F., Collett, T. A., Amberg, W., Roben, P., Binley, J. M., Hoekstra, D., Cababa, D., Jones, T. M., Williamson, R. A., Pilkington, G. R., Haigwood, N. L., Satterthwait, A. C., Sanz, I. and Burton, D. R. (1993) Molecular profile of an antibody response to HIV-1 as probed by combinatorial libraries. *J. Mol. Biol.* 230, 812–823

Bastian, A., Kratzin, H., Eckart, K. and Hilschmann, N. (1992) Intra and Interchain disulfide bridges of the human J chain in secretory Immunonglobulin A. *Biol. Chem. Hoppe-Seylers* 373, 1255–1263

Bukawa, H., Sekigawa, K. I., Hamajima, K., Fukushima, J., Yamada, Y., Kiyono, H. and Okuda, K. Neutralisation of HIV-1 by secretory IgA induced with a new macromolecular multicomponet peptide vaccine candidate. (1995) *Nature Mediceine*: 1, 681–685

Burnett, P. R., VanCott, T. C., Polonis, V. R., Redfield, R. R. and Birx, D. L. (1994) Serum IgA-mediated neutralization of HIV type 1 *J. Immunol.* 152, 4642–4648

Burton, D. R. and Woof, J. M. (1992) Human antibody effector functions. *Adv. Immunol.* 51, 1–84

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Carayannopoulos, L. N., Hexham, J. M. and Capra, J. D. (1996) Localization of the binding site for the monocyte IgA-Fc receptor (CD89) to the domain boundary between Ca2 and Ca3 in human IgA1. *J. Exp. Med.* 183, 1579–1586

Carayannopoulos, L. N., Max, E. E. and Capra, J. D. (1994) Recombinant human IgA expressed in insect cells. *Proc. Natl. Acid. Sci. USA* 91, 8348–8352

Chester, K. A. et al. (1994) Phage libraries for generation of clinically useful antibodies. *Lancet* 343:455–56

Childers, N. K., Bruce, M. G. and McGhee, J. R. (1989) Molecular mechanisms of immunoglobulin A defense. *Ann. Rev. Microbiol.* 43, 503–536

Chintalacharuvu, K. R., Tavill, A. S., Loui, L. N., Vaerman, J. P., Lamm, M. E. and Kaetzel, C. S. (1994) Disulphide bond formation between dimeric IgA and the polymeric immunoglobulin receptor during hepatic transcytosis. *Hepatology* 19, 162–173

Clarkson, A. R., Woodroffe, A. J. Bannister, K. M., Lomax-Smith, J. D. and I, A. (1984) The syndrome of IgA nephropathy. *Clin. Nephrol.* 21, 7–15, Coyne, R. S., Siebrecht, M., Pietsch, M. C. and Casanova, J. E. (1994) Mutational analysis of polymeric immunoglobulin receptor/ligand interactions. *J. Biol. Chem.* 269, 31620–31625

Crowe, J. E., Murphy, B. R., Chanock, R. M., Williamson, R. A., Barbas, C. F. and Burton, D. R. Recombinant human respiratory syncitial virus monoclonal antibody Fab is effective therapeutically when administered directly into the lungs of RSV-infected mice. (1994) *Proc. Natl Acad. Sci. USA*: 91, 1386–1390

Cunningham-Rundles, C. and Lamm, M. E. (1975) Reactive half cystine peptides of the secretory component of human exocrine Immunoglobulin A. *J. Biol. Chem.* 250, 1987–1991

Davis, A. C., Roux, K. H. and Schulman, M. J. (1988) On the structure of polymeric IgM. *Eur. J. Immunol.* 18, 1001–1008

Eiffert, H., Quentin, E., Decker, J., Hillemeir, S., Hufschmidt, M., Klingmuller, D., Weber, M. H. and Hilschmann, N. (1984) Die Primastruktur der menschlichen freien Sekretkomponente und die Anordnung der Disulfidbrucken. *Hoppe-Seylers Z. Physiol Cherm.* 365, 1489–1495

Fallgreen-Gebauer, E., Gebauer, W., Bastian, A., Kratzin, H. D., Eiffert, H., Zimmermann, B., Karas, M. and Hilschman, N. (1993) The covalent linkage of secretory component to IgA. Biol. Chem. *Hoppe-Seyler* 374, 1023–1028

Feng, N., Burns, J. W., Bracy, L. and Greenberg, H. B. Comparison of mucosal and systemic humoral immune responses and subsequent protection in mice orally inoculated with a homologous or a heterologous rotavirus. (1994) *J. Virol.*: 68, 7766–7773

Frutiger, S., Hughes, G. J., Hanly, W. C., Kingzette, M. and Jaton, J. C. (1986) The amino terminal domain of rabbit secretory component is responsible for noncovalent binding to immunoglobulin A dimers. *J. Biol. Chem.* 261, 16673–16681

Garcia-Pardo, A., Lamm, M. E., Plaut, A. G. and Frangione, B. (1981) J chain is covalently bound to both monomer subunits in human secretory IgA. *J. Biol. Chem.* 256, 11734–11738

Gefter et al., Somatic Cell Genet. 3:231–236 (1977)

Goding, 1986, in Monoclonal Antibodies: Principles and Practice, 2d ed., Orlando, Fla., Academic Press, 1986, pp. 60–61, 65–66, 71–74.

Grzych, J. M., Grezel, D., Xu, C., Neyrinck, J. L., Capron, M., Ouma, J. H., Butterworth, A. E. and Capron, A. (1993) IgA antibodies to a protective antigen in human *Schistosoma mansoni. J. Immunol.* 150, 527–535.

Hajishengallis, G., Nikolova, E. and Russell, M. W. (1992) Inhibition of *Streptococcus mutans* adherence to saliva coated hydroxy-apatite by human secretory antibodies to cell surface protein antigen I/II: reversal by IgA protease cleavage. *Infect. Immunol.* 60, 5057–5064

Haseman, C. and Capra, J. D. High-level production of a functional immunoglobulin heterodimer in a baculovirus expression system. (1990) *Proc. Natl. Acad. Sci. USA*: 87, 3942–3946

Hendrickson, B. A., Conner, D. A., Ladd, D. J., Kendall, D., Casanova, J. E., Corthesy, B., Max, E. E., Neutra, M. R., Seidman, C. E. and Seidman, J. G. (1995) Altered hepatic transport of immunoglobulin A in mice lacking the J chain. *J. Exp. Med.* 182, 1905–1911

Hendrickson, B. A., Rindisbacher, L., Corthesy, B., Kendall, D., Waltz, D. A., Neutra, M. R., and Seidman, J. G. (1996) Lack of association of secretory component with IgA in J chain-deficient mice. *J. Immunol.* 157, 750–754

Jewett, A., Giorgi, J. V. and Bonavida, B. (1990) Antibody-dependent cellular cytotoxicity against HIV-coated target cells by peripheral blood monocytes from HIV seropositive asymptomatic patients. J. Immunol. 145, 4065–4071

Jonard, P. P., Rambaud, J. C., Dive, C., Vaerman, J. P., Galian, A. and Delacroix, D. (1984) Secretion of immunoglobulins and plasma proteins from the jejunal mucosa. Transport rate and orgin of polymeric imunoglobulin A. *J. Clif. Inv.* 74, 525–35

Kaetzel, C. S., Robinson, J. K. and Lamm, M. E. (1994) Epithelial transcytosis of monomeric IgA and IgG cross linked through antigen to polymeric IgA. *J. Immunol.* 152, 72–78

Kaetzel. C. S., Robinson, J. K., Chintalacharvuvu, K. R., Vaerman, J. P. and Lamm, M. E. (1991) The polymeric immunoglobulin receptor (secretory component) mediates transport of immune complexes across epithelial cells: A local defense function for IgA. *Pro. Natl. Acad. Sci. USA* 88, 8796–8800

Kamani, N., Krilov, L. R., Wittek, A. E. and Hendry, R. M. (1989) Characterization of the serologic profile of children with human immunodeficiency virus infection: correlation with clinical status. *Clin. Immunol. and Immunopath.* 53, 233–242

Karpas, A., Hill, F., Youle, M., Cullen, V., Gray, J., Byron, N., Hayhoe, F., Tenant-Flowers, M., Howard, L., Gilgen, D., Oates, J. K., Hawkins, D. and Gazzard, B. Effects of passive immunization in patients with the acquired immunodeficiency syndrome-related complex and acquired immunodeficieney syndrome. (1988) *Proc. Natl. Acad. Sci. USA*: 85, 9234–9237

Kaul, T. N., Welliver, R. C. and Ogra, P. L. (1981) Comparison of fluorescent-antibody, neutralizing-antibody, and complement-enhanced neutralizing-antibody assays for detection of serum antibody to respiratory syncytial virus. *J. Clin. Microbiol.* 13: 957–962

Kilian, M., Mestecky, J. and Russell, M. W. (1988) Defense mechanisms involving Fc-dependent functions of immunoglobulin A and their subversion by bacterial immunoglobulin A proteases. *Microbiol. Rev.* 52, 296–303

Kitani, S., Ito, K. and Miyamoto, T. (1985) IgG, IgA, and IgM antibodies to mite in sera and sputa from asthmatic patients. *Ann Allergy* 55, 612–620

Kohler and Milstein, Nature 256:495–497 (1975)

Kohler and Milstein, Eur. J. Immunol. 6:511–519 (1976)

Koshland, M. E. (1985) The coming of age of the immunoglobulin J chain. Ann. Rev. Immunol. 3, 425–453

Kozlowski, P. A. and Jackson, S. Serum IgA subclasses and molecular forms in HIV infection: Selective increases in monomer and apparent restriction of the antibody response to IgA1 antibodies mainly directed at env glycoproteins. (1992) AIDS Res. & Hum. Retrovir.: 8, 1773–1780

Kuhn, L. C. and Kraehenbuhl, J. P. (1979) Interaction of rabbit secretory component with rabbit IgA dimer. J. Biol. Chem. 254, 11066–11071

Kurita, T., Kiyono, H., Komiyama, K., Grossi, C. E., Mestecky, J. and McGhee, J. R. (1986) Isotype-specific immunoregulation; characterization and function of Fc receptors on T-T hybridomas which produce murine IgA-binding factor. J. Immunol. 136, 3953–3960

Lake, D. F., Kawamura, T., Tomiyama, T., Robinson, W. E., Matsumoto, Y. and M, H. E. (1992) Generation and characterization of a human monoclonal antibody that neutralizes diverse HIV-1 isolates in vitro. AIDS 6, 17–24

Lamkhioued, B., Gounni, A. S., Gruart, V., Pierce, A., Capron, A. and Capron, M. (1995) Human eosinophils express a receptor for secretory component. Role in secretory IgA-dependent activation. Eur. J. Immunol. 25, 117–125

Liew, T. N., Russell, S. M., Appleyard, G., Brand, C. M. and Beale, J. (1984) Cross protection in mice infected with influenza virus is correlated with local IgA activity rather than serum antibody or cytotoxic T cell reactivity. Eur. J. Immunol. 14, 350

Lindh, E. and Bjork, I. (1974) Binding of secretory component to dimers of immunoglobulin A in vitro. Eur. J. Biochem. 45, 261–268

Livingston, R. A., Hutton, N., Halsey, N. A., Kline, R. L., Joyner, M. and Quinn, T. C. Human immunodeficiency virus-specific IgA in infants born to human immunodeficiency virus-seropositive women. (1995) Arch. Ped. Adoles. Med.: 149, 503–507

Lucisano-Valim, Y. M. and Lachmann, P. J. (1991) The effect of antibody isotype and antigenic epitope density on the complement-fixing activity of immune complexes: a systematic study using chimaeric anti-NIP antibodies with human Fc regions. Clin. Exp. Immunol. 84, 1–8

Luciw, P. A., Pratt-Lowe, E., Shaw, K. E. S., Levy, J. A. and Cheng-Mayer, C. (1995) Persistent infection of rhesus macaques with T-cell-line-tropic and macrophage-tropic clones of simian/human immunodeficiency viruses (SHIV). Proc. Natl. Accid. Sci USA 92, Maliezewski, C. R., March, C. J, Schoenborn, M. A., Gimpel, S. and Shen, L. (1990) Expression cloning of a human Fc receptor for IgA. J. Exp. Med. 172, 1665–1672

Marx, P. A., Compans, R. W., Gettie, A., Staas, J. K., Gilley, R. M., Mulligan, M. J., Yamshcikov, G. V., Chen, D. and Eldridge, J. H. (1993) Protection against vaginal SIV transmission with microencapsulated vaccine. Science 260, 1323–1327

Matsuda, S., Oka, S., Honda, M., Takebe, Y. and Takemori, T. Characteristics of IgA antibodies against HIV-1 in sera and saliva from HIV seropositive individulas in different clinical stages. (1993) Scand. J. Immunol.: 38, 428–434

Max, E. E. and Korsmeyer, S. J. (1985) Immunoglobulin J chain gene. Structure and expression in B lymphoid cells. J. Exp. Med. 161, 832–849

Mazanec, M. B., Kaetzel, C. S., Lamm, M. E., Fletcher, D. and Nedrud, J. G. (1992) Intracellular neutralization of virus by IgA antibodies. Pro. Natl. Acad. Sci USA 89, 7252–7256

McCafferty J., Griffiths, A. D., Winter, G. and Chiswell D. J. Phage antibodies: filamentous phage displaying antibody variable domains. Nature 348:552–554

Mestecky, J. and McGhee, J. R. (1987) Immunoglobulin A (IgA): molecular and cellular interactions involved in IgA biosynthesis and immune response. Adv. Immunol. 40, 153–245

Miller, C. J., Alexander, N. J., Sutjipto, S., Lackner, A. A., Gettie, A., Hendrikx, A. G., Lowenstein, L. J., Jennings, M. and Marx, P. A. (1989) Genital mucosal transmission of simian immunodeficiency virus: Animal model for heterosexual transmission of human immunodeficiency virus. J. Virol. 63, 4277–4284

Moore, J. P., McKeating, J. A., Norton, W. A. and Sattentau, Q. J. (1991) Direct measurement of soluble CD4 binding to human immunodeficiency virus type 1 virions: gp120 dissociation and its implications for virus-cell binding and fusion reactions and their neutralization by soluble CD4. J. Virol. 65, 1133–1140

Monteiro, R. C., Hostoffer, R. W., Cooper, M. D., Bonner, J. R., Gartland, G. L. and Kubagawa, H. (1993) Definition of immunoglobulin A receptors on eosinophils and their enhanced expression in allergic individuals. J. Clin. Inv. 92, 1681–1685

Monteiro, R. C., Kubagawa, H. and Cooper, M. D. (1990) Cellular distribution, regulation and biochemical nature of an Fcα receptor in humans. J. Exp. Med. 148, 597–613

Moran, M., Andris, J., Matsumato, Y. I., Capra, J. D. and Hersh, E. (1993) Variable region genes of anti HIV human monclonal antibodies: Non-restricted use of the V gene repertoire and extensive somatic mutation. Mol. Immunol. 30, 1543–1551

Mostov, K. E. (1994) Transepithelial transport of immunoglobulins. Ann. Rev. Inmuntol. 12, 63–84

Mostov, K. E. and Blobel, G. (1982) A transmembrane precursor of secretroy component. The receptor for transcellular transport of polymeric immunoglobulins. J. Biol. Chem. 257, 11816–11821

Mostov, K. E. and Deitcher, D. L. (1986) Polymeric immunoglobulin receptor expressed in MDCK cells transcytoses IgA. Cell 46, 613–621

Mostov, K. E., Freidlander, M. and Blobel, G. (1984) The receptor for transepithelial transport of IgA and IgM contains multiple immunoglobulin-like domains. Nature 308, 37–43

O'Reilly, D. R., Miller, L. K. and Luckow, V. A. (1992) Baculovirus expression vectors. A laboratory Manual. W. H. Freeman and Co., New York.

Ogra, P. L., and Karzon, D. T. (1970) The role of immunoglobulins in the mechanism of mucosal immunity to virus infection. Pediatr. Clin. North. Amer. 17: 385–388

Palca, J. (1991) Is the AIDS epidemic slowing! Science 246, 1560

Popper, H., Pongratz, M. and Lanzer, G. (1982) IgA2-alveolitis and eosinophilic pneumonia—a possibly virus-triggered allergy. Allergologia et Immunopathologia. 10, 177–84

Potter, K. N, Li, Y., Pascual, V., Williams, R. C., Byres, L. C., Spellerberg, M., Stevenson, F. K. and Capra, J. D. (1993a) Molecular characterization of a cross-reactive idiotope on human immunoglobulins utilizing the VH4–21 gene segment. J. Exp. Med., 178: 1419–1428

Potter, K. N., Li, Y. and Capra, J. D. (1993b) Antibody production in the baculovirus expression system. Int. Rev. Immunol. 10: 103–112

Putnam, F. W., Liu, Y. S. V. and Low, T. L. K. (1979) Primary structure of a human IgA1 immunoglobulin. J. Biol. Chem. 254, 2865–2874

Re, M., Furlini, G., Vignoli, M., Ricchi, E., Ramazzotti, E., Bianchi, S., Guerra, B., Costigliola, P. and LaPlaca, M. (1992) Vertical transmission of human immunodeficiency virus type I: Prognostic value of IgA antibody to HIV1 polypeptides during pregnancy. *Diagn. Microbiol. Infect. Dis.* 15, 553–556

Roque-Barriera, M. C. and Campos-Neto, A. (1985) Jacalin: an IgA-binding lectin. *J. Immunol.* 134, 1740–1743

Sambrook, J., Fritsch, E. F. and Maniatis T. (1989) *Molecular Cloning: A Laboratory Manual*. Cold Spring Harbor Laboratory Press.

Sawyer, L. A., Katzenstein, D. A., Hendry, R. M., Boone, E. J., Vujcic, L. K., Williams, C. C., Zeger, S. L., Saah, A. J., Rinaldo, C. R., Phair, J. P., Giorgi, J. V. and Quinnan, G. V. (1990) Possible beneficial effects of neutralizing antibodies and antibody-dependent, cell-mediated cytotoxicity in human immunodeficiency virus infection. *AIDS Res. and Human Retroviruses* 6, 341–356

Shen, L., Lasser, R. and Fanger, M. W. (1989) My 43, a monoclonal antibody that reacts with human myeloid cells inhibits monocyte IgA binding and triggers function. *J. Immunol.* 143, 4117–4122

Summers, M. D. and Smith, G. E. (1987) Baculovirus as an expression system. *Tex. Agric Exp. St. Bull.* 1555, 1–56

Tamer, C. S., Lamm, M. E., Robinson, J. K., Piskurich, J. F. and Kaetzel, C. S. (1995) Comparative studies of transcytosis and assembly of secretory IgA in Madin-Darby canine kidney cell expressing human polymeric Ig receptor. *J. Immunol.* 155, 707–714

Tamura, T., Chiba, Y., Chiba, S. and Nakao, T. (1980)Virus excretion and neutralizing antibody response in saliva in human cytomegalovirus infection. *Infect. Immun.* 29: 42–47

Tarkowski, A., Lue, C., Moldoveneau, Z., Kiyono, H., McGhee, J. R. and and Mestecky, J. (1990) Immunization of humans with polysaccharide vaccines induces systemic predominantly IgA2-subclass antibody responses. *J. Immunol.* 144, 3770–3778

Taylor, H. P. and Dimmock, N. J. (1985) Mechanism of neutralization of influenza virus by secretory IgA is different from that of monomeric IgA or IgG. *J. Exp. Med.* 161: 198–205

Torano, A. and Putnam, F. W. (1978) Complete amino acid sequence of the a2 heavy chain of a human IgA2 immunoglobulin of the A2 in (2) allotype. *Proc. Natl. Acad. Sci. USA* 75, 966–969

Tsuzukida, Y., Wang, C. C. and Putnam, F. W. (1979) Structure of the A2m(1) allotype of human IgA-A recombinant molecule. *Proc. Natl. Acad. Sci. USA* 76, 1104–1108

Underdown, B. J. (1990) In *Fc Receptors and tire Action of Antibodies*, ed. Metzger, H. (American Society for Microbiology, Washington D.C.), pp. 74–93

Underdown, B. J. and Schiff, J. M. (1986) Immunoglobulin A: strategic defense initiative at the mucosal surface. *Ann. Rev. Immunol.* 4, 389–417

Underdown, B. J., De Rose, J. and Plaut, A. (1977) Disulfide bonding of secretory component to a single monomer subunit in human secretory IgA. *J. Immunol* 118, 1816–1821

Vittecoq. D., Chevret, S., Morand-Joubert, L., Heshmati, F., Audat, F., Bary, M., Dusautior, T., Bismuth, A., Viard, J. P., Barre-Sinoussi, F., Bach, J. F. and Lefrere, J. J. (1995) Passive immunotherapy in AIDS: A double-blind study based on transfusions of plasma rich in anti-human immunodeficiency virus 1 antibodies vs. transfusions of seronegative plasma. *Proc. Natl. Acad. Sci. USA* 92, 1195–1199

Vittecoq, D., Chevret, S., Morand-Joubert, L., Heshmati, F., Audat, F., Bary, M., Dusautior, T., Bismuth, A., Viard, J. P., Barre-Sinoussi, F., Bach, J. F. and Lefrere, J. J. Passive immunotherapy in AIDS: A double-blind study based on transfusions of plasma rich in anti-human immunodeficiency virus 1 antibodies vs. transfusions of seronegative plasma. (1995) *Proc. Natl. Acad. Sci. USA*: 92, 1195–1199

Wang, Y., Ben, K., Cao, X. and Wang, Y. (1996) Transport of anti-sperm monoclonal IgA and IgG into murine male and female genital tracts from blood. Effect of sex hormones. *J. Immunol.* 156, 1014–1019

Weisbart, R. H., Kacena, A., Schuh, A. and Golde, D. W. (1988) GM-CSF induces human neutrophil IgA-mediated phagocytosis by an IgA Fc receptor activation mechanism. *Nature* 332, 647–648

Winter, G., Griffiths, A. D., Hawkins, R. E. and Hoogenboom, H. R. (1994) Making Antibodies by Phage Display Technology. *Ann Rev Immunol.* 12:433–55

Yao, Q. Y., Rowe, M., Morgan, A. J., Sam, C. K., Prasad, U., Dang, Y. and Rickinson, A. J. (1991) The Epstein-Barr virus carrier state: dominance of a single growth-transforming isolate in the blood and in the oropharynx of healthy virus carriers. *Int. J. Cancer* 48: 45–49

Zikan, J., Mestecky, J., Kulhavy, R. and Bennet, J. C. (1986) The stochiometry of J chain in human dimeric IgA. *Mol. Immunol.* 23, 541–544

What is claimed is:

1. A mini-IgA antibody comprising a VH domain fused to a first IgA1 C$\alpha$3 domain including a tailpiece, and a VL domain fused to a second IgA1 C$\alpha$3 domain including a tailpiece, wherein said VL and VH domains constitute an antigen or hapten recognition site, and wherein said mini-IgA antibody lacks other C$\alpha$ domains.

2. A dimeric IgA antibody comprising two mini-IgA antibodies of claim 1 connected by a J-chain.

3. The antibody of claim 2 dispersed in a pharmaceutically acceptable solution.

4. The antibody of claim 1, wherein said C$\alpha$3 domains are human C$\alpha$3 domains.

5. The antibody of claim 1, wherein said antigen is a viral, bacterial or protozoan antigen.

6. The antibody of claim 5, wherein said antigen is a virus.

7. The antibody of claim 6, wherein said virus is influenza A, B or C, parainfluenza, paramyxovirus, Newcastle disease virus, respiratory syncytial virus, measles, mumps, adenovirus, adenoassociated virus, parvovirus, Epstein-Barr virus, rhinovirus, coxsackievirus, echovirus, reovirus, rhabdovirus, lymphocytic choriomeningitis, coronavirus, poliovirus, herpes simplex, human immunodeficiency virus, cytomegalovirus, papillomavirus, virus B, varicella-zoster, poxvirus, rubella, rabies, picornavirus or rotavirus.

8. The antibody of claim 7, wherein said virus is a human immunodeficiency virus.

9. The antibody of claim 8, wherein said antibody is immunoreactive with gp120 of HIV.

10. The antibody of claim 7, wherein said virus is an influenza A virus.

11. The antibody of claim 7, wherein said virus is an influenza B virus.

12. The antibody of claim 7, wherein said virus is an influenza C virus.

13. The antibody of claim 7, wherein said virus is a parainfluenza virus.

14. The antibody of claim 7, wherein said virus is a paramyxovirus.

15. The antibody of claim 7, wherein said virus is a Newcastle disease virus.

16. The antibody of claim 7, wherein said virus is a respiratory syncytial virus.

17. The antibody of claim 7, wherein said virus is a measles virus.

18. The antibody of claim 7, wherein said virus is a mumps virus.

19. The antibody of claim 7, wherein said virus is an adenovirus.

20. The antibody of claim 7, wherein said virus is an adenoassociated virus.

21. The antibody of claim 7, wherein said virus is a parvovirus.

22. The antibody of claim 7, wherein said virus is an Epstein-Barr virus.

23. The antibody of claim 7, wherein said virus is a rhinovirus.

24. The antibody of claim 7, wherein said virus is a coxsackievirus.

25. The antibody of claim 7, wherein said virus is an echovirus.

26. The antibody of claim 7, wherein said virus is a reovirus.

27. The antibody of claim 7, wherein said virus is a rhabdovirus.

28. The antibody of claim 7, wherein said virus is a lymphocytic choriomeningitis virus.

29. The antibody of claim 7, wherein said virus is a coronavirus.

30. The antibody of claim 7, wherein said virus is a poliovirus.

31. The antibody of claim 7, wherein said virus is a herpes simplex virus.

32. The antibody of claim 7, wherein said virus is a cytomegalovirus.

33. The antibody of claim 7, wherein said virus is a papillomavirus.

34. The antibody of claim 7, wherein said virus is a virus B.

35. The antibody of claim 7, wherein said virus is a varicella-zoster virus.

36. The antibody of claim 7, wherein said virus is a poxvirus.

37. The antibody of claim 7, wherein said virus is a rubella virus.

38. The antibody of claim 7, wherein said virus is a rabies virus.

39. The antibody of claim 7, wherein said virus is a picornavirus.

40. The antibody of claim 7, wherein said virus is a rotavirus.

41. The antibody of claim 5, wherein said antigen is a bacteria.

42. The antibody of claim 41, wherein said bacteria is pneumococci, *Streptococcus pyogenes, Streptococcus agalactiae, Streptococcus equi, Streptococcus canis, Streptococcus bovis, Streptococcus equinus, Streptococcuts anginosus, Streptococcus sanguis, Streptococcus salivarius, Streptococclts mitis, Streptococcus mutans*, viridans streptococci, peptostreptococci, *Enterococcus faecalis, Enterococcus faecium, Staphylococcus epidennidis, Staphylococcus aureus, Hemophilus influenzae, Pseudomonas aeruginosa, Pseudomonas pseudomallei, Pseudomonas mallei, Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi, Listeria monocytogenes, Nocordia asteroides*, Actinomycetes, *Treponema pallidum*, Leptospirosa, *Klebsiella pneumoniae, Escherichia coli*, Proteus, Serratia, Acinetobacter, *Yersinia pestis, Francisella tulrensis*, Enterobacter, Bacteriodes or Legionella.

43. The antibody of claim 41, wherein said bacteria is a pneumococci.

44. The antibody of claim 41, wherein said bacteria is a *Streptococcus pyogenes.*

45. The antibody of claim 41, wherein said bacteria is a *Streptococus agalactiae.*

46. The antibody of claim 41, wherein said bacteria is a *Streptococcus equi.*

47. The antibody of claim 41, wherein said bacteria is a *Streptococcus canis.*

48. The antibody of claim 41, wherein said bacteria is a *Streptococcus bovis.*

49. The antibody of claim 41, wherein said bacteria is a *Streptococcus equoius.*

50. The antibody of claim 41, wherein said bacteria is a *Streptococcus anginosus.*

51. The antibody of claim 41, wherein said bacteria is a *Streptococcus sanguis.*

52. The antibody of claim 41, wherein said bacteria is a *Streptococcus salivarius.*

53. The antibody of claim 41, wherein said bacteria is a *Streptococcus mitis.*

54. The antibody of claim 41, wherein said bacteria is a *Streptococcus mutans.*

55. The antibody of claim 41, wherein said bacteria is a viridans streptococci.

56. The antibody of claim 41, wherein said bacteria is a peptostreptococci.

57. The antibody of claim 41, wherein said bacteria is a *Enterococcus faecalis.*

58. The antibody of claim 41, wherein said bacteria is a *Enterococcus faecium.*

59. The antibody of claim 41, wherein said bacteria is a *Staphylococcus epidermidis.*

60. The antibody of claim 41, wherein said bacteria is a *Staphylococcits aureus.*

61. The antibody of claim 41, wherein said bacteria is a *Hemophilus influenzae.*

62. The antibody of claim 41, wherein said bacteria is a *Pseudomonas aeruginosa.*

63. The antibody of claim 41, wherein said bacteria is a *Pseudomonas pseudomallei.*

64. The antibody of claim 41, wherein said bacteria is a *Pseudomonas mallei.*

65. The antibody of claim 41, wherein said bacteria is a *Brucella melitensis.*

66. The antibody of claim 41, wherein said bacteria is a *Brucella suis.*

67. The antibody of claim 41, wherein said bacteria is a *Brucella abortus.*

68. The antibody of claim 41, wherein said bacteria is a *Bordetella pertussis.*

69. The antibody of claim 41, wherein said bacteria is a *Neisseria meningitidis.*

70. The antibody of claim 41, wherein said bacteria is a *Neisseria gonorrhoeae.*

71. The antibody of claim 41, wherein said bacteria is a *Moraxella catarrrhalis.*

72. The antibody of claim 41, wherein said bacteria is a *Corynebacterium diphtheriae.*

73. The antibody of claim 41, wherein said bacteria is a *Corynebacterium ulcerans*.

74. The antibody of claim 41, wherein said bacteria is a *Corynebacterium pseudotuberculosis*.

75. The antibody of claim 41, wherein said bacteria is a *Corynebacterium pseudodiphtheriticum*.

76. The antibody of claim 41, wherein said bacteria is a *Corynebacterium urealyticum*.

77. The antibody of claim 41, wherein said bacteria is a *Corynebacterium hemolyticum*.

78. The antibody of claim 41, wherein said bacteria is a *Corynebacterium equi*.

79. The antibody of claim 41, wherein said bacteria is a *Listeria monocytogenes*.

80. The antibody of claim 41, wherein said bacteria is a *Nocordia asteroices*.

81. The antibody of claim 41, wherein said bacteria is an *Actinomycetes*.

82. The antibody of claim 41, wherein said bacteria is a *Treponema pallidum*.

83. The antibody of claim 41, wherein said bacteria is a Leptospirosa.

84. The antibody of claim 41, wherein said bacteria is a *Klebsiella pneumoniae*.

85. The antibody of claim 41, wherein said bacteria is a *Escherichia coli*.

86. The antibody of claim 41, wherein said bacteria is a Proteus.

87. The antibody of claim 41, wherein said bacteria is a Serratia.

88. The antibody of claim 41, wherein said bacteria is an Acinetobacter.

89. The antibody of claim 41, wherein said bacteria is a *Yersinia pestis*.

90. The antibody of claim 41, wherein said bacteria is a *Francisella tularensis*.

91. The antibody of claim 41, wherein said bacteria is a Enterobacter.

92. The antibody of claim 41, wherein said bacteria is a Bacteriodes.

93. The antibody of claim 41, wherein said bacteria is a Legionella.

94. The antibody of claim 5, wherein said antigen is a protozoan.

95. The antibody of claim 94, wherein said protozoan is a Cryptosporidium.

96. The antibody of claim 94, wherein said protozoan is an *Isospora belli*.

97. The antibody of claim 94, wherein said protozoan is a *Toxoplasma gondii*.

98. The antibody of claim 94, wherein said protozoan is a *Trichomonas vaginalis*.

99. The antibody of claim 94, wherein said protozoan is a Cyclospora.

100. The antibody of claim 94, wherein said protozoan is a *Chlamydia trachomatis*.

101. The antibody of claim 94, wherein said protozoan is a *Chlamydia psittaci*.

102. The antibody of claim 94, wherein said protozoan is a *Chlamydia pneumoniae*.

* * * * *

UNITED STATES PATENT AND TRADEMARK OFFICE
CERTIFICATE OF CORRECTION

PATENT NO.    : 6,063,905
DATED         : May 16, 2000
INVENTOR(S)   : J. Donald Capra et al.

It is certified that error appears in the above-identified patent and that said Letters Patent is hereby corrected as shown below:

<u>Title page,</u>
Item [56], OTHER PUBLICATIONS, please delete "Quirakkoo" and insert therefor -- Guirakkoo --; and please add the following references:

Bakos, M., Kurowsky, A. and Goldblum, R.M. (1991) Characterization of a critical binding site for human polymeric Ig on secretory component. *J. Immunol.* 147, 3419-3426.

Bakos, M., Kurowsky, A., Woodward, C.S., Denney, R.M. and Goldblum, R.M. (1991b) Probing the topography of free and polymeric Ig-bound human secretory component with monoclonal antibodies. *J. Immunol.* 146, 162,-168.

Barbas, C.F., Bjorling, E., Chiodi, F., Dunlop, N., Cababa, D., Jones, T.M., Zebedee, S.L., Persson, M.A.A., Nara, P.L., Norrby, E. and Burton, D.R. (1992) Recombinant human Fab fragments neutralise human type 1 immunodeficiency virus *in vitro*. *Proc. Natl Acad. Sci. USA* 89, 9339-9343.

Barbas, C.F., Collett, T.A., Amberg, W., Roben, P., Binley, J.M., Hoekstra, D., Cababa, D., Jones, T.M., Williamson, R.A., Pilkington, G.R., Haigwood, N.L., Satterthwait, A.C., Sanz, I. and Burton, D.R. (1993) Molecular profile of an antibody response to HIV-1 as probed by combinatorial libraries. *J. Mol. Biol.* 230, 812-823.

Bastian, A., Kratzin, H., Eckart, K. and Hilschmann, N. (1992) Intra and Interchain disulfide bridges of the human J chain in secretory Immunonglobulin A. *Biol. Chem. Hoppe-Seylers* 373, 1255-1263.

Bukawa, H., Sekigawa, K.I., Hamajima, K., Fukushima, J., Yamada, Y., Kiyono, H. and Okuda, K. Neutralisation of HIV-1 by secretory IgA induced with a new macromolecular multicomponet peptide vaccine candidate. (1995) *Nature Mediceine* : 1, 681-685.

Burnett, P.R., VanCott, T.C., Polonis, V.R., Redfield, R.R. and Birx, D.L. (1994) Serum IgA-mediated neutralization of HIV type1. *J. Immunol.* 152, 4642-4648.

Burton, D.R. and Woof, J.M. (1992) Human antibody effector function. *Adv. Immunol.* 51, 1-84.

Carayannopoulos, L.N., Hexham, J.M. and Capra, J.D. (1996) Localization of the binding site for the monocyte IgA-Fc receptor (CD89) to the domain boundary between Cx2 and Cx3 in human IgA1. *J. Exp. Med.* 183, 1579-1586.

Carayannopoulos, L.N., Max, E.E. and Capra, J.D. (1994) Recombinant human IgA expressed in insect cells. *Proc. Natl. Acad. Sci. USA* 91, 8348-8352.

UNITED STATES PATENT AND TRADEMARK OFFICE
CERTIFICATE OF CORRECTION

PATENT NO.    : 6,063,905
DATED         : May 16, 2000
INVENTOR(S)   : J. Donald Capra et al.

It is certified that error appears in the above-identified patent and that said Letters Patent is hereby corrected as shown below:

Chester, K.A. *et al.* (1994) Phage libraries for generation of clinically useful antibodies. *Lancet* 343:455-56.

Childers, N.K., Bruce, M.G. and McGhee, J.R. (1989) Molecular mechanisms of immunoglobulin A defense. *Ann. Rev. Microbiol.* 43, 503-536.

Chintalacharuvu, K.R., Tavill, A.S., Loui, L.N., Vaerman, J.P., Lamm, M.E. and Kaetzel, C.S. (1994) Disulphide bond formation between dimeric IgA and the polymeric immunoglobulin receptor during hepatic transcytosis. *Hepatology* 19, 162-173.

Clarkson, A.R., Woodroffe, A.J. Bannister, K.M., Lomax-Smith, J.D. and I, A. (1984) The syndrome of IgA nephropathy. *Clin. Nephrol.* 21, 7-14.

Coyne, R.S., Siebrecht, M., Pietsch, M.C. and Casanova, J.E. (1994) Mutational analysis of polymeric immunoglobulin receptor/ligand interactions. *J. Biol. Chem.* 269, 31620-31625.

Crowe, J.E., Murphy, B.R., Chanock, R.M., Williamson, R.A., Barbas, C.F. and Burton, D.R. Recombinant human respiratory syncitial virus monoclonal antibody Fab is effective therapeutically when administered directly into the lungs of RSV-infected mice. (1994) *Proc. Natl Acad. Sci. USA* : 91, 1386-1390.

Cunningham-Rundles, C. and Lamm, M.E. (1975) Reactive half cystine peptides of the secretory component of human exocrine Immunoglobulin A. *J. Biol. Chem.* 250, 1987-1991.

Eiffert, H., Quentin, E., Decker, J., Hillemeir, S., Hufschmidt, M., Klingmuller, D., Weber, M.H. and Hilschmann, N. (1984) Die Primastruktur der menschlichen freien Sekretkomponente und die Anordnung der Disulfidbrucken. *Hoppe-Seylers Z. Physiol Chem.* 365, 1489-1495.

Fallgreen-Gebauer, E., Gebauer, W., Bastian, A., Kratzin, H.D., Eiffert, H., Zimmermann, B., Karas, M. and Hilschman, N. (1993) The covalent linkage of secretory component to IgA. *Biol. Chem. Hoppe-Seyler* 374, 1023-1028.

Feng, N., Burns, J.W., Bracy, L. and Greenberg, H.B. Comparison of mucosal and systemic humoral immune responses and subsequent protection in mice orally inoculated with a homologous or a heterologous rotavirus. (1994) *J. Virol.* : 68, 7766-7773.

Frutiger, S., Hughes, G.J., Hanly, W.C., Kingzette, M. and Jaton, J.C. (1986) The amino terminal domain of rabbit secretory component is responsible for noncovalent binding to immunoglobulin A dimers. *J. Biol. Chem.* 261, 16673-16681.

UNITED STATES PATENT AND TRADEMARK OFFICE
CERTIFICATE OF CORRECTION

PATENT NO.    : 6,063,905
DATED         : May 16, 2000
INVENTOR(S)   : J. Donald Capra et al.

It is certified that error appears in the above-identified patent and that said Letters Patent is hereby corrected as shown below:

Garcia-Pardo, A., Lamm, M.E., Plaut, A.G. and Frangione, B. (1981) J chain is covalently bound to both monomer subunits in human secretory IgA. *J. Biol. Chem.* 256, 11734-11738.

Gefter *et al.*, "A Simple Method for Polyethylene Glycol-Promoted Hybridization of Mouse Myeloma Cells," Somatic Cell Genet. 3:231-236, 1977.

Grzych, J.M., Grezel, D., Xu, C., Neyrinck, J.L., Capron, M., Ouma, J.H., Butterworth, A.E. and Capron, A. (1993) IgA antibodies to a protective antigen in human Schistosoma mansoni. *J. Immunol.* 150, 527-535.

Hajishengallis, G., Nikolova, E. and Russell, M.W. (1992) Inhibition of *Streptococcus mutans* adherence to saliva coated hydroxy-apatite by human secretory antibodies to cell surface protein antigen I/II: reversal by IgA protease cleavage. *Infect. Immunity.* 60, 5057-5064.

Haseman, C. and Capra, J.D. High-level production of a functional immunoglobulin heterodimer in a baculovirus expression system. (1990) *Proc. Natl. Acad. Sci. USA* : 87, 3942-3946.

Hendrickson, B.A., Conner, D.A., Ladd, D.J., Kendall, D., Casanova, J.E., Corthesy, B., Max, E.E., Neutra, M.R., Seidman, C.E. and Seidman, J.G. (1995) Altered hepatic transport of immunoglobulin A in mice lacking the J chain. *J. Exp. Med.* 182, 1905-1911.

Hendrickson, B.A., Rindisbacher, L., Corthesy, B., Kendall, D., Waltz, D.A., Neutra, M.R., and Seidman, J.G. (1996) Lack of association of secretory component with IgA in J chain-deficient mice. *J. Immunol.* 157, 750-754.

Jewett, A., Giorgi, J.V. and Bonavida, B. (1990) Antibody-dependent cellular cytotoxicity against HIV-coated target cells by peripheral blood monocytes from HIV seropositive asymptomatic patients. *J. Immunol.* 145, 4065-4071.

Jonard, P.P., Rambaud, J.C., Dive, C., Vaerman, J.P., Galian, A. and Delacroix, D. (1984) Secretion of immunoglobulins and plasma proteins from the jejunal mucosa. Transport rate and orgin of polymeric imunoglobulin A. *J. Clin. Inv.* 74, 525-35.

Kaetzel, C.S., Robinson, J.K. and Lamm, M.E. (1994) Epithelial transcytosis of monomeric IgA and IgG cross linked through antigen to polymeric IgA. *J. Immunol.* 152, 72-76.

UNITED STATES PATENT AND TRADEMARK OFFICE
CERTIFICATE OF CORRECTION

PATENT NO.   : 6,063,905
DATED        : May 16, 2000
INVENTOR(S)  : J. Donald Capra et al.

It is certified that error appears in the above-identified patent and that said Letters Patent is hereby corrected as shown below:

Kaetzel, C.S., Robinson, J.K., Chintalacharvuvu, K.R., Vaerman, J.P. and Lamm, M.E. (1991) The polymeric immunoglobulin receptor (secretory component) mediates transport of immune complexes across epithelial cells: A local defense function for IgA. *Pro. Natl. Acad. Sci. USA* 88, 8796-8800.

Karpas, A., Hill, F., Youle, M., Cullen, V., Gray, J., Byron, N., Hayhoe, F., Tenant-Flowers, M., Howard, L., Gilgen, D., Oates, J.K., Hawkins, D. and Gazzard, B. Effects of passive immunization in patients with the acquired immunodeficiency syndrome-related complex and acquired immunodeficiency syndrome. (1988) *Proc. Natl. Acad. Sci. USA* : 85, 9234-9237.

Kaul, T.N., Welliver, R.C. and Ogra, P.L. (1981) Comparison of fluorescent-antibody, neutralizing-antibody, and complement-enhanced neutralizing-antibody assays for detection of serum antibody to respiratory syncytial virus. *J. Clin. Microbiol.* 13: 957-962.

Kilian, M., Mestecky, J. and Russell, M.W. (1988) Defense mechanisms involving Fc-dependent functions of immunoglobulin A and their subversion by bacterial immunoglobulin A proteases. *Microbiol. Rev.* 52, 296-303.

Kitani, S., Ito, K. and Miyamoto, T. (1985) IgG, IgA, and IgM antibodies to mite in sera and sputa from asthmatic patients. *Ann Allergy* 55, 612-620.

Kuhn, L.C. and Kraehenbuhl, J.P. (1979) Interaction of rabbit secretory component with rabbit IgA dimer. *J. Biol. Chem.* 254, 11066-11071.

Kurita, T., Kiyono, H., Komiyama, K., Grossi, C.E., Mestecky, J. and McGhee, J.R. (1986) Isotype-specific immunoregulation; characterization and function of Fc receptors on T-T hybridomas which produce murine IgA-binding factor. *J. Immunol.* 136, 3953-3960.

Lake, D.F., Kawamura, T., Tomiyama, T., Robinson, W.E., Matsumoto, Y. and M, H.E. (1992) Generation and characterization of a human monoclonal antibody that neutralizes diverse HIV-1 isolates *in vitro*. *AIDS* 6, 17-24.

Lamkhioued, B., Gounni, A.S., Gruart, V., Pierce, A., Capron, A. and Capron, M. (1995) Human eosinophils express a receptor for secretory component. Role in secretory IgA-dependent activation. *Eur. J. Immunol.* 25, 117-125.

Liew, T.N., Russell, S.M., Appleyard, G., Brand, C.M. and Beale, J. (1984) Cross protection in mice infected with influenza virus is correlated with local IgA activity rather than serum antibody or cytotoxic T cell reactivity. *Eur. J. Immunol.* 14, 350.

UNITED STATES PATENT AND TRADEMARK OFFICE
CERTIFICATE OF CORRECTION

PATENT NO. : 6,063,905
DATED : May 16, 2000
INVENTOR(S) : J. Donald Capra et al.

It is certified that error appears in the above-identified patent and that said Letters Patent is hereby corrected as shown below:

Lindh, E. and Bjork, I. (1974) Binding of secretory component to dimers of immunoglobulin A in vitro. *Eur. J. Biochem.* 45, 261-268.

Livingston, R.A., Hutton, N., Halsey, N.A., Kline, R.L., Joyner, M. and Quinn, T.C. Human immunodeficiency virus-specific IgA in infants born to human immunodeficiency virus-seropositive women. (1995) *Arch. Ped. Adoles. Med.* : 149, 503-507.

Lucisano-Valim, Y.M. and Lachmann, P.J. (1991) The effect of antibody isotype and antigenic epitope density on the complement-fixing activity of immune complexes: a systematic study using chimaeric anti-NIP antibodies with human Fc regions. *Clin. Exp. Immunol.* 84, 1-8.

Luciw, P.A., Pratt-Lowe, E., Shaw, K.E.S., Levy, J.A. and Cheng-Mayer, C. (1995) Persistent infection of rhesus macaques with T-cell-line-tropic and macrophage-tropic clones of simian/human immunodeficiency viruses (SHIV). *Proc. Natl. Acad. Sci USA,* 7490-7494, 1992..

Maliezewski, C.R., March, C.J, Schoenborn, M.A., Gimpel, S. and Shen, L. (1990) Expression cloning of a human Fc receptor for IgA. *J. Exp. Med.* 172, 1665-1672.

Marx, P.A., Compans, R.W., Gettie, A., Staas, J.K., Gilley, R.M., Mulligan, M.J., Yamshcikov, G.V., Chen, D. and Eldridge, J.H. (1993) Protection against vaginal SIV transmission with microencapsulated vaccine. *Science* 260, 1323-1327.

Matsuda, S., Oka, S., Honda, M., Takebe, Y. and Takemori, T. Characteristics of IgA antibodies against HIV-1 in sera and saliva from HIV seropositive individulas in different clinical stages. (1993) *Scand. J. Immunol.* : 38, 428-434.

Max, E.E. and Korsmeyer, S.J. (1985) Immunoglobulin J chain gene. Structure and expression in B lymphoid cells. *J. Exp. Med.* 161, 832-849.

Mazanec, M.B., Kaetzel, C.S., Lamm, M.E., Fletcher, D. and Nedrud, J.G. (1992) Intracellular neutralization of virus by IgA antibodies. *Pro. Natl. Acad. Sci USA* 89, 6901-6905.

McCafferty J., Griffiths, A.D., Winter, G. and Chiswell D.J. Phage antibodies: filamentous phage displaying antibody variable domains. *Nature* 348:552-554.

Mestecky, J. and McGhee, J.R. (1987) Immunoglobulin A (IgA): molecular and cellular interactions involved in IgA biosynthesis and immune response. *Adv. Immunol.* 40, 153-245.

UNITED STATES PATENT AND TRADEMARK OFFICE
CERTIFICATE OF CORRECTION

PATENT NO. : 6,063,905
DATED : May 16, 2000
INVENTOR(S) : J. Donald Capra et al.

It is certified that error appears in the above-identified patent and that said Letters Patent is hereby corrected as shown below:

Miller, C.J., Alexander, N.J., Sutjipto, S., Lackner, A.A., Gettie, A., Hendrikx, A.G., Lowenstein, L.J., Jennings, M. and Marx, P.A. (1989) Genital mucosal transmission of simian immunodeficiency virus: Animal model for heterosexual transmission of human immunodeficiency virus. *J. Virol.* 63, 4277-4284.

Moore, J.P., McKeating, J.A., Norton, W.A. and Sattentau, Q.J. (1991) Direct measurement of soluble CD4 binding to human immunodeficiency virus type 1 virions: gp120 dissociation and its implications for virus-cell binding and fusion reactions and their neutralization by soluble CD4. *J. Virol.* 65, 1133-1140.

Monteiro, R.C., Hostoffer, R.W., Cooper, M.D., Bonner, J.R., Gartland, G.L. and Kubagawa, H. (1993) Definition of immunoglobulin A receptors on eosinophils and their enhanced expression in allergic individuals. *J. Clin. Inv.* 92, 1681-1685.

Monteiro, R.C., Kubagawa, H. and Cooper, M.D. (1990) Cellular distribution, regulation and biochemical nature of an Fcα receptor in humans. *J. Exp. Med.* 171, 597-613.

Moran, M., Andris, J., Matsumato, Y.I., Capra, J.D. and Hersh, E. (1993) Variable region genes of anti HIV human monclonal antibodies: Non-restricted use of the V gene repertoire and extensive somatic mutation. *Mol. Immunol.* 30, 1543-1551.

Mostov, K.E. (1994) Transepithelial transport of immunoglobulins. *Ann. Rev. Immunol.* 12, 63-84.

Mostov, K.E. and Blobel, G. (1982) A transmembrane precursor of secretory component. The receptor for transcellular transport of polymeric immunoglobulins. *J. Biol. Chem.* 257, 11816-11821.

Mostov, K.E. and Deitcher, D.L. (1986) Polymeric immunoglobulin receptor expressed in MDCK cells transcytoses IgA. *Cell* 46, 613-621.

Mostov, K.E., Freidlander, M. and Blobel, G. (1984) The receptor for transepithelial transport of IgA and IgM contains multiple immunoglobulin-like domains. *Nature* 308, 37-43.

Ogra, P.L., and Karzon, D.T. (1970) The role of immunoglobulins in the mechanism of mucosal immunity to virus infection. *Pediatr. Clin. North. Amer.* 17: 385-400.

Potter, K.N, Li, Y., Pascual, V., Williams, R.C., Byres, L.C., Spellerberg, M., Stevenson, F.K. and Capra, J.D. (1993a) Molecular characterization of a cross-reactive idiotope on human immunoglobulins utilizing the VH4-21 gene segment. *J. Exp. Med.,* 178: 1419-1428.

UNITED STATES PATENT AND TRADEMARK OFFICE
CERTIFICATE OF CORRECTION

PATENT NO.    : 6,063,905
DATED         : May 16, 2000
INVENTOR(S)   : J. Donald Capra et al.

It is certified that error appears in the above-identified patent and that said Letters Patent is hereby corrected as shown below:

Putnam, F.W., Liu, Y.S.V. and Low, T.L.K. (1979) Primary structure of a human IgA1 immunoglobulin. *J. Biol. Chem.* 254, 2865-2874.

Re, M., Furlini, G., Vignoli, M., Ricchi, E., Ramazzotti, E., Bianchi, S., Guerra, B., Costigliola, P. and LaPlaca, M. (1992) Vertical transmission of human immunodeficiency virus type I: Prognostic value of IgA antibody to HIV1 polypeptides during pregnancy. *Diagn. Microbiol. Infect. Dis.* 15, 553-556.

Roque-Barriera, M.C. and Campos-Neto, A. (1985) Jacalin: an IgA-binding lectin. *J. Immunol.* 134, 1740-1743.

Sawyer, L.A., Katzenstein, D.A., Hendry, R.M., Boone, E.J., Vujcic, L.K., Williams, C.C., Zeger, S.L., Saah, A.J., Rinaldo, C.R., Phair, J.P., Giorgi, J.V. and Quinnan, G.V. (1990) Possible beneficial effects of neutralizing antibodies and antibody-dependent, cell-mediated cytotoxicity in human immunodeficiency virus infection. *AIDS Res. and Human Retroviruses* 6, 341-356.

Shen, L., Lasser, R. and Fanger, M.W. (1989) My 43, a monoclonal antibody that reacts with human myeloid cells inhibits monocyte IgA binding and triggers function. *J. Immunol.* 143, 4117-4122.

Tamer, C.S., Lamm, M.E., Robinson, J.K., Piskurich, J.F. and Kaetzel, C.S. (1995) Comparative studies of transcytosis and assembly of secretory IgA in Madin-Darby canine kidney cell expressing human polymeric Ig receptor. *J. Immunol.* 155, 707-714.

Tamura, T., Chiba, Y., Chiba, S. and Nakao, T. (1980)Virus excretion and neutralizing antibody response in saliva in human cytomegalovirus infection. *Infect. Immun.* 29: 842-845.

Tarkowski, A., Lue, C., Moldoveneau, Z., Kiyono, H., McGhee, J.R. and and Mestecky, J. (1990) Immunization of humans with polysaccharide vaccines induces systemic predominantly IgA2-subclass antibody responses. *J. Immunol.* 144, 3770-3778.

Taylor, H.P. and Dimmock, N.J. (1985) Mechanism of neutralization of influenza virus by secretory IgA is different from that of monomeric IgA or IgG. *J. Exp. Med.* 161: 198-209.

Torano, A. and Putnam, F.W. (1978) Complete amino acid sequence of the a2 heavy chain of a human IgA2 immunoglobulin of the A2 in (2) allotype. *Proc. Natl. Acad. Sci. USA* 75, 966-969.

Tsuzukida, Y., Wang, C.C. and Putnam, F.W. (1979) Structure of the A2m(1) allotype of human IgA-A recombinant molecule. *Proc. Natl. Acad. Sci. USA* 76, 1104-1108.

UNITED STATES PATENT AND TRADEMARK OFFICE
CERTIFICATE OF CORRECTION

PATENT NO. : 6,063,905
DATED : May 16, 2000
INVENTOR(S) : J. Donald Capra et al.

It is certified that error appears in the above-identified patent and that said Letters Patent is hereby corrected as shown below:

Underdown, B.J. and Schiff, J.M. (1986) Immunoglobulin A: strategic defense initiative at the mucosal surface. *Ann. Rev. Immunol.* 4, 389-417.

Underdown, B.J., De Rose, J. and Plaut, A. (1977) Disulfide bonding of secretory component to a single monomer subunit in human secretory IgA. *J. Immunol* 118, 1816-1821.

Vittecoq, D., Chevret, S., Morand-Joubert, L., Heshmati, F., Audat, F., Bary, M., Dusautior, T., Bismuth, A., Viard, J.P., Barre-Sinoussi, F., Bach, J.F. and Lefrere, J.J. (1995) Passive immunotherapy in AIDS: A double-blind study based on transfusions of plasma rich in anti-human immunodeficiency virus 1 antibodies vs. transfusions of seronegative plasma. *Proc. Natl. Acad. Sci. USA* 92, 1195-1199.

Wang, Y., Ben, K., Cao, X. and Wang, Y. (1996) Transport of anti-sperm monoclonal IgA and IgG into murine male and female genital tracts from blood. Effect of sex hormones. *J. Immunol.* 156, 1014-1019.

Weisbart, R. H., Kacena, A., Schuh, A. and Golde, D.W. (1988) GM-CSF induces human neutrophil IgA-mediated phagocytosis by an IgA Fc receptor activation mechanism. *Nature* 332, 647-648.

Yao, Q.Y., Rowe, M., Morgan, A.J., Sam, C.K., Prasad, U., Dang, Y. and Rickinson, A.J. (1991) Salivary and Serum IgA Antibodies to the Epstein-Barr Virus Glycoprotein gp340: Incidence and Potential for Virus Neutralization.. *Int. J. Cancer* 48: 45-50.

Zikan, J., Mestecky, J., Kulhavy, R. and Bennet, J.C. (1986) The stochiometry of J chain in human dimeric IgA. *Mol. Immunol.* 23, 541-544.

Column 31,
Line 60, please delete "epidennidis" and insert therefor -- epidermidis --.

Column 32,
Line 20, please delete "equoius" and insert therefor --equinus --.

Signed and Sealed this

Twenty-second Day of April, 2003

JAMES E. ROGAN
*Director of the United States Patent and Trademark Office*